United States Patent [19]
Vallee

[11] Patent Number: 5,162,203
[45] Date of Patent: Nov. 10, 1992

[54] METHODS OF MEASURING ISOZYMES AND ISOZYME CLASSES OF ALCOHOL DEHYDROGENASE

[75] Inventor: Bert L. Vallee, Brookline, Mass.

[73] Assignee: President and Fellows of Harvard College, Cambridge, Mass.

[21] Appl. No.: 404,218

[22] Filed: Sep. 7, 1989

[51] Int. Cl.$^5$ .................. C12Q 1/32; C12Q 1/02; G01N 33/48; C12N 9/04

[52] U.S. Cl. .................. 435/26; 435/4; 435/25; 435/29; 435/190; 435/968; 435/973; 436/63; 436/140; 436/811; 436/815; 436/904

[58] Field of Search .................. 435/4, 26, 190, 25, 435/29, 968, 973; 436/63, 140, 172, 811, 815, 904

[56] References Cited
PUBLICATIONS

Bernhard et al., Biochemistry 907:185-192 (1970).
Deetz et al., Biochemistry 23:6882-6828 (1984).
Mårdh et al., PNAS (USA) 82:4979-4982 (1985).
Ibid., 83:8908-8912 (Dec. 1986).
Vallee et al., 1983, Isozymes: Current Topics in Biological and Medical Research, Liss, pp. 219-244, New York.
Montavon et al., Anal. Biochem. 176:48-56 (1989).
Wagner et al., Biochemistry 22:1857-1863 (1983).
Wagner et al., Biochemistry 23:2193-2199 (1984).
Ditlow et al., Biochemistry 23:6363-6368 (1984).
Strydom et al., Anal. Biochem. 123:422-429 (1982).
Mårdh et al., Biochemistry, 25:7279-7282 (1986).
Kaiser et al., Biochemistry 27:1132-1140 (1988).
Mårdh et al., Proc. Natl. Acad. Sci. USA 23:2836-2840 (1986).
Consalvi et al., Biochem. Biophys. Res. Commun. 139:1009-1016 (1986).
Vallee, Therap. Notes 73:71-74 (1966).
Bohman, Arch. Gen. Psychiat. 35:269-276 (1978).
Skursky et al., Drug and Alcohol Dependence 6:187-190 (1980).
Skursky et al., Anal. Biochem. 99:65-71 (1979).
Agarwal et al., Fresenius Anal. Chem. 311:374 (1982).
Kato et al., Clin. Chem. 30:1817-1820 (1984).
Khayrollah et al., Anal. Clin. Biochem. 19:35-42 (1982).
Keung et al., Anal. Biochem. 151:92-96 (1985).
Bosron et al., Biochemistry 18:1101-1105 (1979).
Dafeldecker and Vallee, J. Prot. Chem. 1:59 (1982).
Wierzchowski et al., 1989 Anal. Biochem. 178:57-62 (1989).

Primary Examiner—Margaret Moskowitz
Assistant Examiner—Stephanie W. Zitomer
Attorney, Agent, or Firm—Allegretti & Witcoff, Ltd.

[57] ABSTRACT

The present invention provides fluorescence-based methods for sensitively detecting total ADH activity in human sera and selectively measuring the activity of different classes of ADH in human sera and other body fluids and tissues. The present invention also provides highly purified Class I, Class II, and Class III isozymes, and methods for their purifiation. The class of substrates consisting of various naphthaldehydes and quinoline aldehydes provide the requisite sensitivity and selectivity for measurements of the activity of ADH and individual ADH classes. These fluorescence-based methods may serve as a diagnostic aid in disease assessment, in particular, diagnosis of alcohol abuse, alcoholism, alcohol consumption, altered alcohol sensitivity or tolerance.

16 Claims, 10 Drawing Sheets

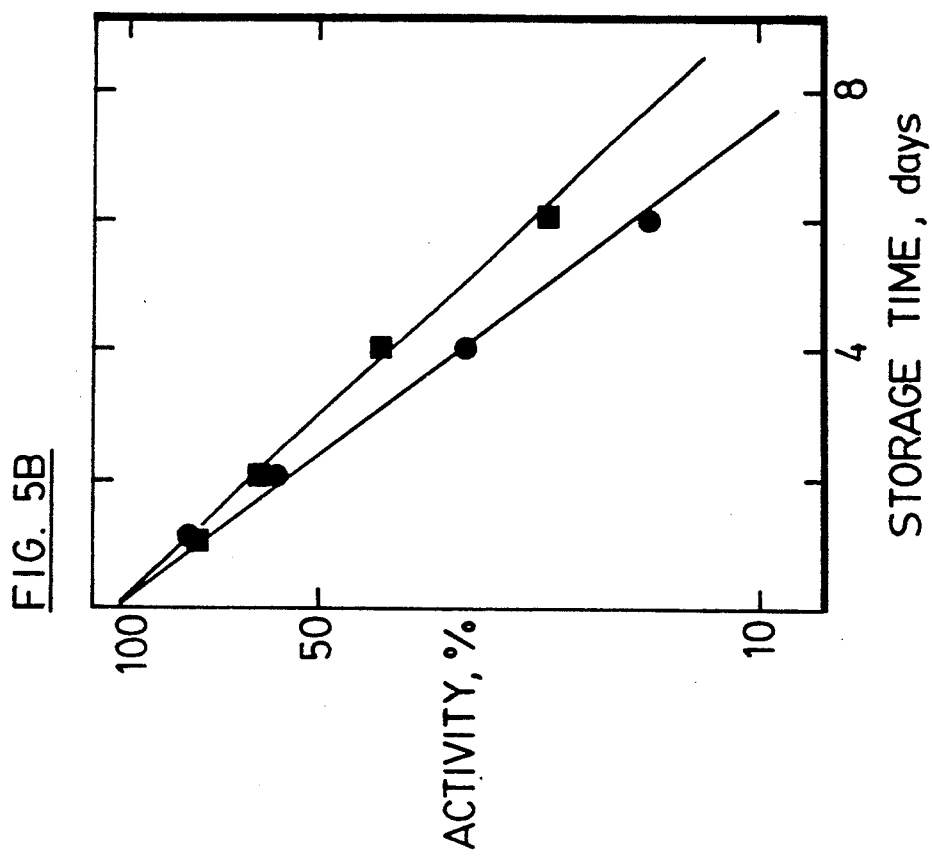
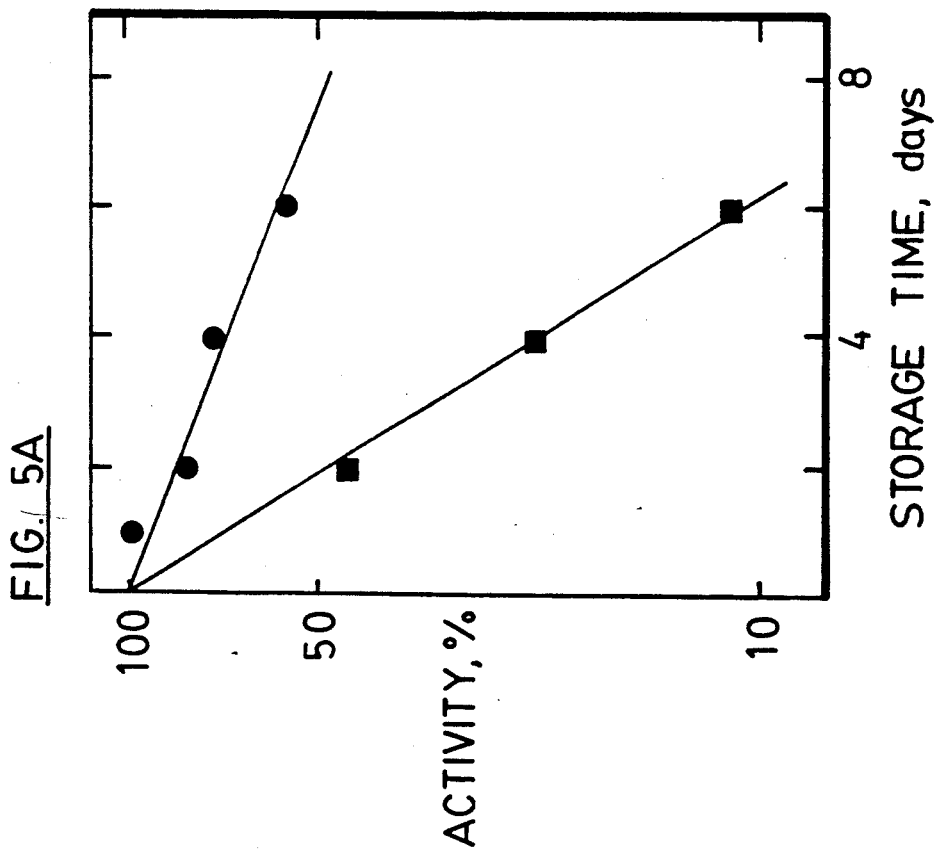
FIG. 5B
FIG. 5A

METHODS OF MEASURING ISOZYMES AND ISOZYME CLASSES OF ALCOHOL DEHYDROGENASE

BACKGROUND OF THE INVENTION

Human alcohol dehydrogenase (ADH, EC 1.1.1.1) is the primary enzyme responsible for ethanol metabolism in humans. ADH exists as 3 classes, Class I, II, III, that can be isolated from liver and have been differentiated on the basis of their electrophoretic (Vallee et al., 1983, Isozymes: Current Topics in Biological & Medical Research pp. 219-244, Liss, New York), immunological (Montavon et al., 1989, Anal Biochem 176 48-56), catalytic (Wagner, et al, 1983, Biochemistry 22: 1857-1863; Wagner et al., 1984. Biochemistry 23: 2193-2199; Ditlow et al., 1984, Biochemistry 23: 6363-6368), and structural (Strydom et al., 1982, Anal. Biochem. 123: 422-429; Kaiser et al, 1988, Biochemistry 27: 1132-1140) differences. The ADH classes further contain isozymes, particularly Class I ADH. Class I isozymes include homodimers and heterodimers composed of $\alpha$, $\beta$ and $\gamma$ subunits, for example, $\alpha\beta_1$, $\alpha\gamma_1$, $\beta_1\beta_1$, $\beta_1\gamma_1$, $\beta_1\gamma_2$ and $\gamma_1\gamma_1$. The occurrence of particular isozymes in some tissues is remarkably selective For example, Class III ($\chi$) ADH is the only isozyme in brain and placenta and virtually the only isozyme in testis, while Class II ($\eta$) has only been observed in liver homogenates. Vallee et al., 1983, supra. Since liver ADH isozymes are clearly responsible for the oxidation of most of the ethanol ingested, their involvement in the physiological and pathological consequences of human ethanol consumption is of considerable interest.

The classes of ADH, as well as individual isozymes differ in their substrate and inhibitor specificities. Wagner et al, 1983, Biochemistry 22: 1857-63; Deetz et al., 1984, Biochemistry 23 6822-28; Ditlow et al., 1984, Biochemistry 23: 6863-68; Mårdh et al., 1985, Proc. Natl. Acad. Sci. USA 83: 2836-40. For example differences in activity toward a number of aromatic alcohols and aldehydes in norepinephrine (Mårdh et al., 1986, Proc. Natl. Acad Sci. USA 83: 8908-12; Mårdh et al., 1985, Proc. Natl. Acad. Sci. USA, 82: 4979-4982), dopamine (Mårdh et al., 1986, Biochemistry, 25: 7279-7282) and serotonin metabolism (Consalvi et al., 1986, Biochem. Biophys. Res. Commun., 139: 1009-1016) have been observed. However, these or other substrates capable of measuring ADH activity cannot differentiate among classes, isozymes, or phenotypic ADH variants of isozymes. For this reason, investigations of the function of human ADH have long been hindered by the lack of sensitive and specific assays to detect the activity of and characterize the individual forms of ADH in human body fluids and tissues. The capacity to accomplish this would advance studies of their distribution and regulation and might help to elucidate genetic factors underlying alcohol use and abuse. Vallee, 1966, Therap. Notes 73: 71-4. There is increasing evidence of a genetic predisposition to certain forms of chronic alcoholism (Bohman. 1978, Arch. Gen. Psychiat. 35: 269-276).

Little is known at present regarding the genetics and distribution of the three ADH classes let alone the manner in which any differences between them might be manifested metabolically. It would clearly be advantageous if their existence, preponderance and variability could be ascertained in vivo from accessible tissues and body fluids The detection of ADH activity in such tissues or fluids has proven exceedingly difficult.

Total ADH activity in serum has been measured previously using a variety of substrates and methods but none of them have been specific or selective for isozymes or isozyme classes. Purified human isozymes or isozyme classes in fact have not been available for calibration or control and efforts to achieve indirect differentiation of Class II from Class I activity in serum and tissues based on differential pyrazole inactivation have only been inferential. Skursky et al., 1980, Drug and Alcohol Dependence, 6: 187-190.

Several assays for ADH activity have been developed to study its distribution in tissues and body fluids with the objective of determining possible prognostic and/or diagnostic characteristics Skursky et al., 1979, Anal. Biochem., 99: 65-71; Agarwal et al, 1982, Fresenius Anal. Chem. 311: 314., Kato et al., 1984, Clin Chem, 30: 1817-1820. Using conventional assay methods based on NAD reduction ADH activity is virtually undetectable in the serum of normal individuals. Thus, efforts to employ serum ADH for differential diagnostic purposes have been quite disappointing and conclusions regarding the usefulness of increased ADH activity to assess common types of liver disease remain in question. Khayrollah et al., 1982 Anal. Clin. Biochem., 19: 35-42. In addition any ADH activity measurements thus far reported are measurements of undifferentiated ADH activity, i.e., the sum of all activities of isozymes present Conventional methods, therefore, lack sufficient sensitivity to routinely detect ADH activity in normal sera and sufficient specificity or selectivity to measure the activities of different ADH isozyme classes in serum or other body fluids and tissues. The present invention solves these problems by providing for the first time, assay methods that are both sensitive enough to detect levels of ADH activity in sera and other body fluids and tissues, and, more importantly, selective enough to differentiate Class I from Class II ADH activity in such body fluids or tissues. The present invention also provides for the first time, highly purified human ADH isozymes and isozyme classes as standards for calibration and controls of enzyme activity in the novel assay methods of the present invention. In particular, highly purified cofactor-free Class I isozymes are recovered in greater yield and with higher specific activities as compared to corresponding isozymes prepared by conventional methods.

SUMMARY OF THE INVENTION

The present invention provides fluorescence-based methods for sensitively detecting levels of ADH activity in human sera and selectively measuring the activity of different classes of ADH in human sera and other body fluids and tissues. The present invention also provides highly purified Class I, Class II, and Class III isozymes, and methods for their purification. The class of substrates consisting of various naphthaldehydes and quinoline aldehydes provide the requisite sensitivity and selectivity for measurements of total ADH activity and the activity of individual ADH classes. In particular, the compounds 4-methoxy-1-naphthaldehyde and 6-methoxy-2-naphthaldehyde are preferred as sensitive substrates of ADH, highly selective for Classes I and II ADH, respectively. The activity of Class I and Class II ADH can now be measured in serum in the subnanomolar range using these substrates in the presence or absence of a class-selective inhibitor by the novel methods here presented.

In particular, the present invention provides methods for the sensitive, accurate and direct measurement of Class II ADH activity in serum or other body fluids and tissues in the presence or absence of significant amounts of Class I ADH. Both a two-assay and four-assay procedure are described for the selective measurement of Class I and Class II ADH activity. These fluorescence-based methods may serve as a diagnostic aid in disease assessment, in particular the present invention comprehends diagnostic test kits comprising ADH class-selective substrates and inhibitors. Diagnosis of alcohol abuse alcoholism, altered alcohol sensitivity, altered alcohol tolerance and alcohol consumption are made possible by methods of the present invention.

BRIEF DESCRIPTION OF THE DRAWINGS

FIG. 5A and 5B are graphs showing the effect of serum storage at 4° C. (circles) or at room temperature (squares) on the measured activity of Class I (FIG. 5A) and Class II (FIG. 5B) ADH in a representative serum sample.

BRIEF DESCRIPTION OF THE PREFERRED EMBODIMENT

Figure 1A:
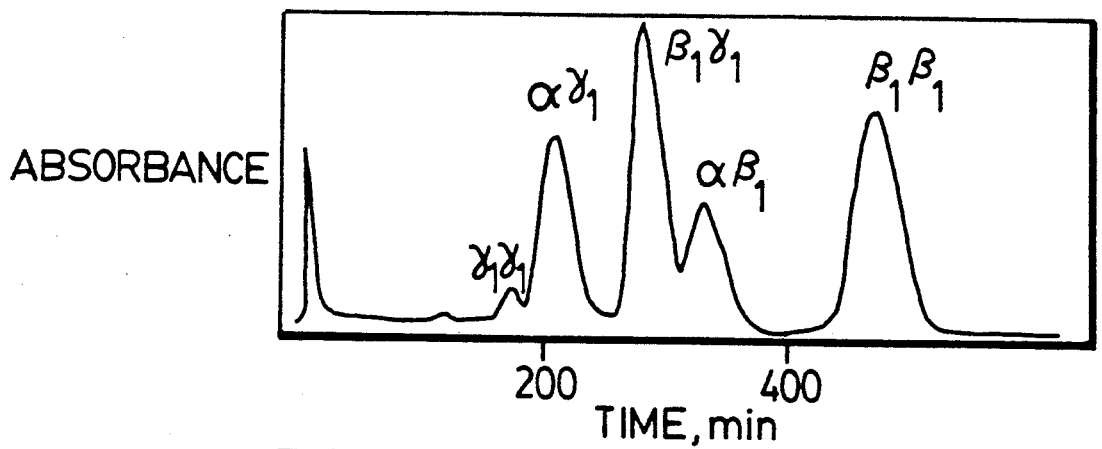
FIG. 1A, 1B and 1C are HPLC chromatographs from the semi-preparative analysis of bulk Class I ADH liver isozymes from individuals of 3 different ADH phenotypes: $\alpha$, $\beta_1$, $\gamma_1$ (FIG. 1A); $\alpha$, $\beta_1$, $\gamma_2$ (FIG. 1B); and $\alpha$, $\beta_1$, $\beta_2$, $\gamma_1$, $\gamma_2$ (FIG. 1C).

Most methods of detecting ADH activity are based on the following reversible enzyme reaction catalyzed by ADH:

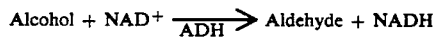

Alcohol + NAD$^+$ $\xrightarrow{\text{ADH}}$ Aldehyde + NADH

There are a number of conventional methods for detecting ADH activity. Many methods assay the oxidation of ethanol by measuring the increase or decrease of NADH by measuring absorption at 340 nm Other methods measure the reduction of the strongly colored substrate p-nitrosodimethylaniline (NDMA) to the colorless hydroxylamine derivative. None of these conventional methods, however, are able to differentiate and thus selectively measure the activity of ADH isozyme classes in serum or other body fluids or tissues. In contrast to such conventional methods, the present invention permits such differentiation and thus selective measurement. The present invention provides sensitive and specific assays for Class I and Class II ADH isozyme activities.

The present invention also provides highly purified human ADH isozymes and isozyme classes. Such purified isozymes are necessary for calibration and controls of enzyme activity in assay methods of the present invention which permit the differential measurement of Class I and Class II activities in tissues and body fluids such as serum. For example, human liver ADH Class I isozymes had been partially purified by a previously described protocol (Wagner et al., 1983, Biochemistry 22: 1857–1863). In the present invention, these isozymes were purified to homogeneity by Affi-Gel Blue absorption and HPLC cation-exchange chromatography. Class I ADH, consisting of the $\alpha$, $\beta$, and $\gamma$ subunit types and the allelic variants $\beta_1$, $\beta_2$, $\beta_3$, $\gamma_1$, and $\gamma_2$ in homodimeric and heterodimeric combination, were initially isolated as a complex mixture of the structurally related isozymes which were further fractionated by cation-exchange chromatography in the presence of NAD+. Individual isozymes isolated by this conventional chromatography, although apparently homogeneous by starch and urea polyacrylamide gel electrophoresis, eluted as multiple peaks when subsequently applied to cation-exchange HPLC. Spectrophotometric analyses revealed that the coenzyme NADH or one of its decomposition products, when bound to an ADH isozyme, was the cause of the multiple peaks observed. Consequently, bound coenzyme was removed by treatment of ADH-containing fractions with Affi-Gel Blue affinity resin prior to HPLC analysis. Individual isozymes treated by this method eluted as single peaks from HPLC. These cofactor-free Class I isozymes were recovered in greater yield and with high specific activities as compared with the corresponding isozymes prepared by conventional chromatography. For example, specific activities using conventional assays for ethanol oxidation at pH 10 ranged from 0.42 U/mg for $\beta_1\beta_1$ to 4.4 U/mg for $\gamma_1\gamma_1$ ADH. Example 1 describes the purification of ADH isozymes in detail, including the semi-preparative scale isolation of individual Class I ADH isozymes from a mixture of α, β, and γ homodimers and heterodimers as shown in FIGS. 1 and 2. Thus, the procedures of Example 1 make possible the rapid purification of milligram quantities of individual ADH isozymes with high specific activities for studies of isozyme-specific structural and functional characteristics, as well as for use in the calibration of and controls for the assay methods of the present invention. The purified biologically-active isozymes were also useful in the reconstitution experiments with inactive human sera described in Example 3.

The present invention provides sensitive and highly selective methods for detecting the activity of Class I and II ADH isozymes in serum or other body fluids or tissues by using class-specific or class selective substrates and inhibitors. The methods rely on measuring the rate of reduction of certain naphthaldehyde and quinoline aldehyde compounds. These compounds have never before been recognized or used as class-selective ADH substrates. The activity of ADH isozyme classes in serum and other body fluids or tissues is determined by measuring the rate of reduction of these novel class-selective ADH substrates in the presence or absence of class-selective inhibitors. Class I selective inhibitors, for example, include 4-methyl and 4-ethyl pyrazole.

Because ADH is the principal enzyme responsible for ethanol oxidation in humans, its actions and properties are fundamentally related also to the pathologic effects of ethanol and to alcohol abuse or alcoholism itself. Alcohol abuse is a heterogeneous set of behaviors that induces any pattern of ethyl alcohol intake that causes medical and/or social complications. Within any particular family the syndrome is often similar in its pattern and severity. However, families differ in both genetic and sociocultural background, so the causes of the family differences remain ambiguous. In summary, it has been difficult to unravel the etiology and underlying mechanisms of this condition owing to the complex interrelationship among behavioral psychosocial, and biologic determinants. However, predisposing biologic factors undoubtedly exist, as exemplified by studies of alcohol abuse in the adopted children of alcoholics. Cloninger et al., 1981, Arch. Gen. Psychiat 33: 861-68. In fact, two subtypes of alcohol abuse were identified, type I (milieu-limited) and type II (male-limited). Type II was shown to be highly heritable in men. Cloninger et al., supra.

In addition to such predisposing biological factors, ethanol-metabolizing capacity and the molecular heterogeneity of liver ADH appear to be under genetic control. Class II ADH, in particular, may serve a unique role in the elimination of ethanol since its $K_m$ for ethanol is significantly higher (as much as 100 times) than that of other ADH isozymes. In this regard, considerable variability in increased Class II activity as a function of time after alcohol consumption has been found in preliminary studies of groups of individuals undergoing alcohol tolerance tests. Thus, the fluorescence-based methods of the present invention are useful in the diagnosis of altered alcohol tolerance and alcohol consumption. The frequency of increased serum ADH activity, in particular Class II ADH activity, has been found in preliminary studies to be higher in alcoholics than in the normal population. Therefore, the fluorescence-based methods of the present invention are also useful in the diagnosis of alcohol abuse, alcoholism or predisposition to alcoholism.

ADH catalyzes the reversible enzyme reaction shown above using NAD+/NADH as the enzyme cofactor. The forward reaction wherein alcohols may be oxidized to aldehydes via NAD+ takes place under certain assay conditions (e.g., pH ~10.0). Many conventional ADH assays are performed under conditions which favor this forward reaction. In contrast, the present invention involves methods which employ assay conditions (e.g., pH ~7.0) that favor the reverse reaction (i.e., aldehydes reduced to alcohols via NADH).

The rate of conversion of aldehyde to alcohol is proportional to the quantity of ADH present in the sample to be assayed. The rate of disappearance of a fluorescent substrate or appearance of a fluorescent product as assayed by methods of the present invention is, therefore proportional to the amount of ADH present.

The present invention relies on a class of substrates consisting of naphthaldehydes and quinoline aldehydes in the presence or absence of alkyl-pyrazole inhibitors, in order to provide the requisite sensitivity for improved serum measurements and the specificity or selectivity for determination of Class I and Class II activities in serum or other body fluids or tissues.

Accordingly, the method of the present invention may employ aldehyde compounds of the formula:

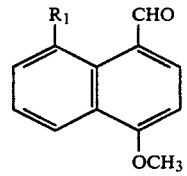
I wherein $R_1$ is —OH, —OCH$_3$, —N(CH$_3$)$_2$, or —O(CH$_2$)$_n$CH$_3$ and n is an integer from 1-8; when $R_1$ is H, the compound is 4-methoxy-1-naphthaldehyde and is designated substrate IA herein:

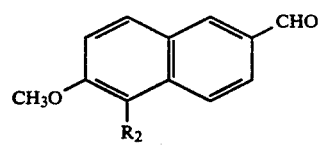
II wherein $R_2$ is —H, —OH, —OCH$_3$, —N(CH$_3$)$_2$, or —O(CH$_2$)$_n$CH$_3$ and n is an integer from 1-8; when $R_2$ is H, the compound is 6-methoxy-2-naphthaldehyde and is designated substrate IIA herein;

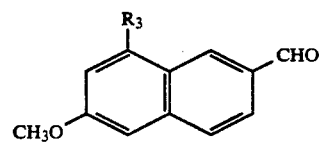
III wherein $R_3$ is —H, —OH, —OCH$_3$, —N(CH$_3$)$_2$, or —O(CH$_2$)$_n$CH$_3$ and n is an integer from 1-8;

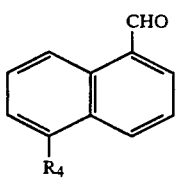

IV wherein $R_4$ is —H, —OH, —OCH$_3$, —N(CH$_3$)$_2$, or —O(CH$_2$)$_n$CH$_3$ and n is an integer from 1-8;

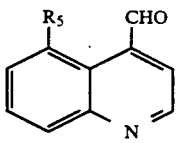

V wherein $R_5$ is —H, —OH, —OCH$_3$, —N(CH$_3$)$_2$, or —O(CH$_2$)$_n$CH$_3$ and n is an integer from 1-8;

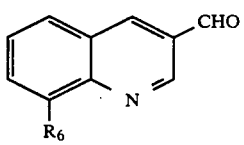

VI wherein $R_6$ is —H, —OH, —OCH$_3$, —N(CH$_3$)$_2$, or —O(CH$_2$)$_n$CH$_3$ and n is an integer from 1-8;

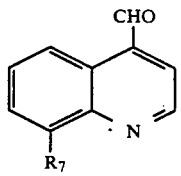

VII wherein $R_7$ is —H, —OH, —OCH$_3$, —N(CH$_3$)$_2$, or —O(CH$_2$)$_n$CH$_3$ and n is an integer from 1-8;

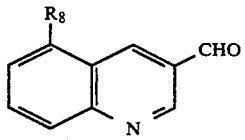

VIII wherein $R_8$ is —H, —OH, —OCH$_3$, —N(CH$_3$)$_2$, or —O(CH$_2$)$_n$CH$_3$ and n is an integer from 1-8.

In addition to compounds of the structures drawn above a variety of alkyl-substituted naphthaldehydes (e.g. at one or more of carbons 1-8) and alkyl-substituted quinoline aldehydes (e.g. at one or more of carbons 2-8) may be suitable as substrates with enhanced specificity or selectivity for ADH isozymes.

4-Methoxy-1-naphthaldehyde (substrate IA) and 6-methoxy-2-naphthaldehyde (substrate IIA) are selective, sensitive substrates for ADH Classes I and II, respectively, exhibiting differential substrate preferences for ADH Classes I and II. Fluorescence-based assays of the present invention employing these compounds are both more sensitive and specific than conventional ADH activity assays, including those assays based on NADH absorbance or fluorescence. Theorell et. al., 1954 Acta Scand., 8: 1490-91. The present invention utilizes these differential substrate preferences along with class-selective inhibitors to allow the determination of subnanomolar amounts of Class I and II ADH present in human serum or other body fluids or tissue.

The spectral parameters for 4-methoxy-1-naphthaldehyde (IA), 6-methoxy-2-naphthaldehyde (IIA) and their reduction products (IB and IIB, respectively) are shown in Table I.

TABLE I

Spectral Parameters for Absorption and Fluorescence of Selective ADH Substrates and Products in Aqueous Media[a]

| Compound | Absorption | | Fluorescence | |
|---|---|---|---|---|
| | $\lambda_{max}$ (nm) | $\epsilon_{max}$ (M$^{-1}$cm$^{-1}$) | $\lambda_{max}$ (nm) | $\phi$ |
| ADH Substrates (Aldehydes) | | | | |
| IA | 332 | 13,100 | 420 | 0.003 |
| IIA | 315 | 14,400 | 450 | 0.22 |
| | | | 435 | 0.03[b] |
| ADH Products (Alcohols) | | | | |
| IB | 297 | 5,400 | 370 | 0.36 |
| IIB | 329 | 1,250 | 355 | 0.26 |

[a]Mes buffer (45 mM), pH 7.0.
[b]In methanol.

Figure 3A:
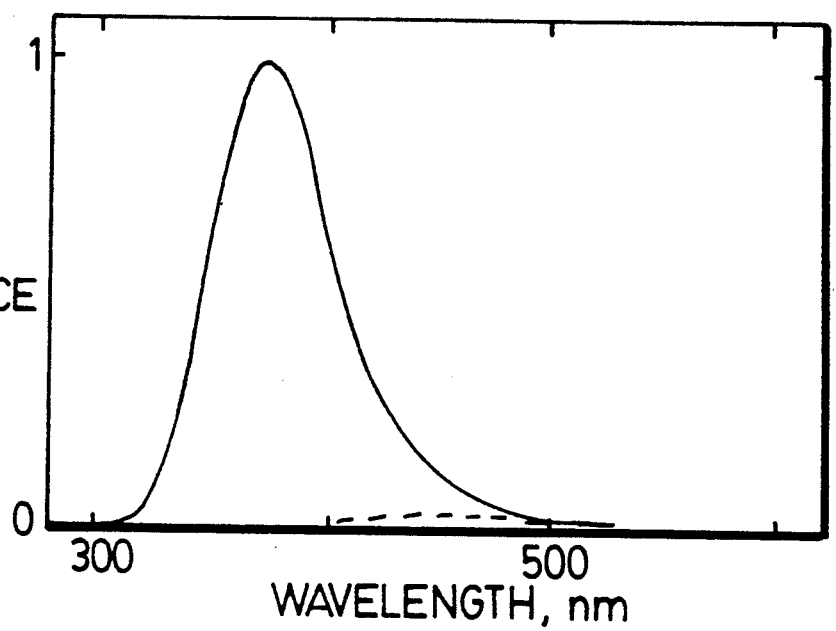
FIG. 3A and 3B are graphs of the fluorescence spectra of preferred ADH substrates IA (FIG. 3A, dashed line) and IIA (FIG. 3B. dashed line), and products IB (FIG. 3A, solid line) and IIB (FIG. 3B, solid line).
Figure 3B:
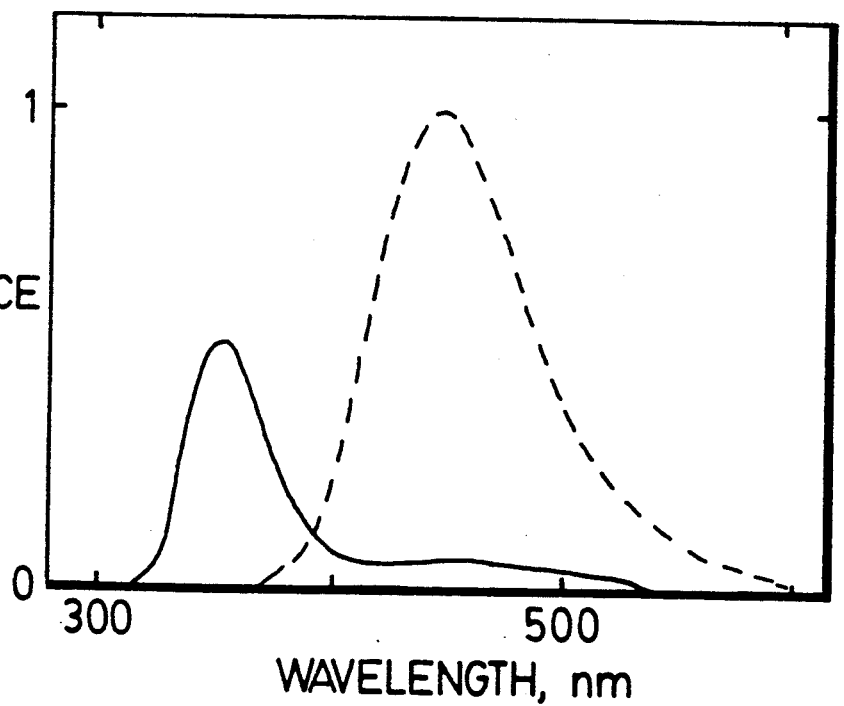
Figure 4A:
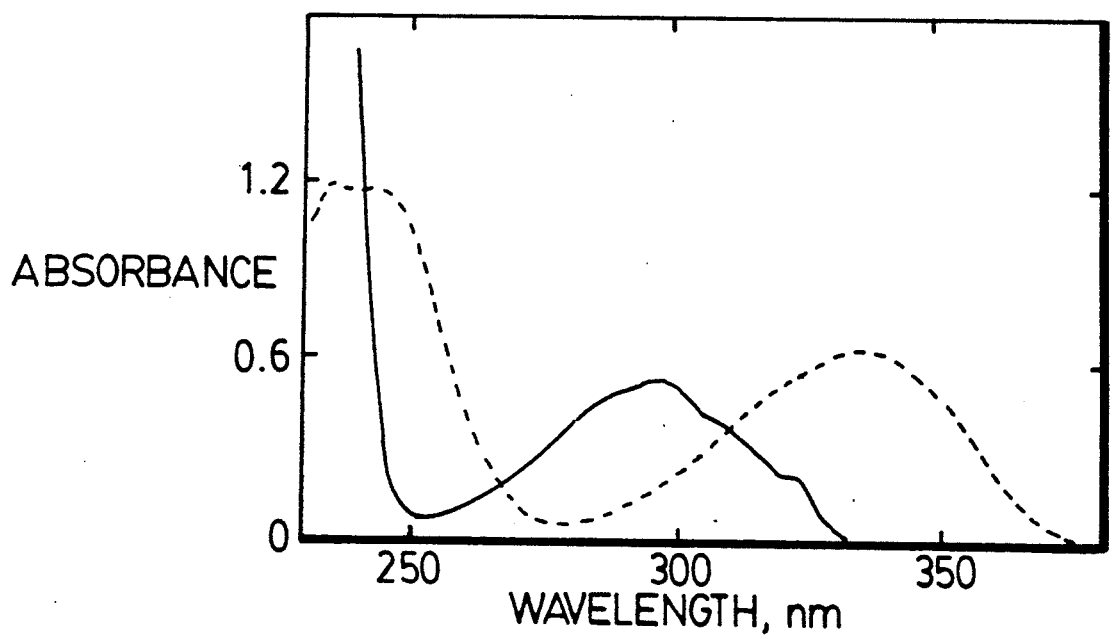
FIG. 4A and 4B are graphs of ultraviolet absorption spectra of the same ADH substrates and products as in FIG. 3A and 3B.
Figure 4B:
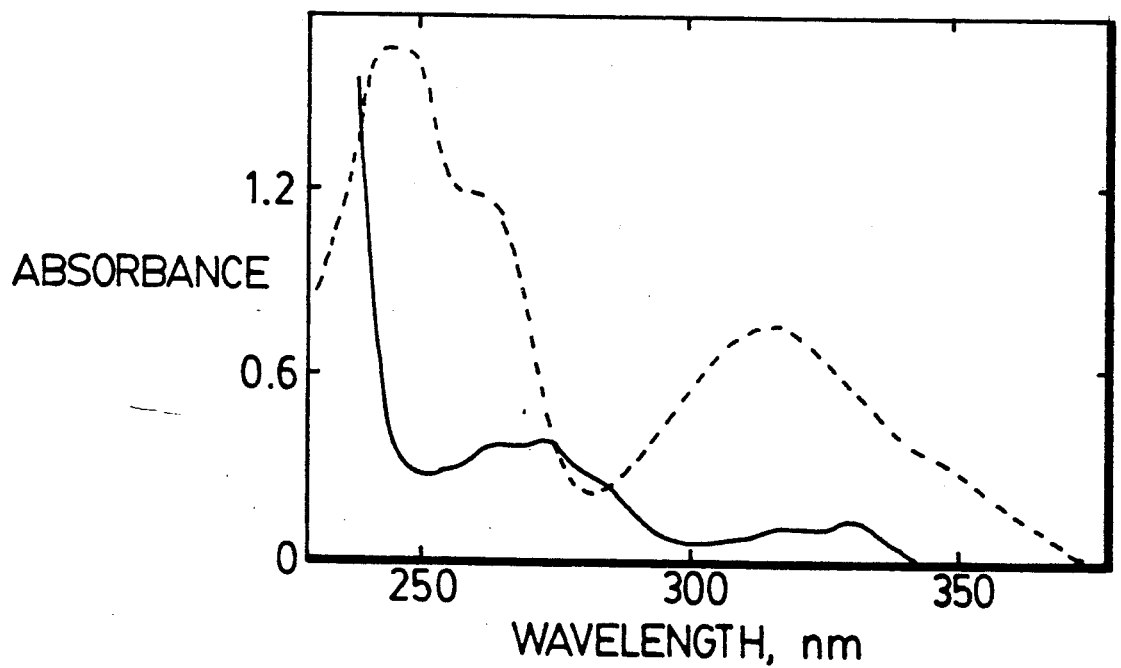

FIGS. 3A and 3B are graphs of the fluorescence spectra before (dashed line) and after (solid line) the enzymatic reduction of substrate IA (FIG. 3A) and substrate IIA (FIG. 3B) measured at excitation wavelengths of 299 and 310 nm, respectively. The reaction mixtures contained 10 μM NADH and 5-8 nM $\alpha\beta_1$ ADH in 50 mM Mes buffer pH 7.15. The fluorescence quantum yield of substrate IA is low (FIG. 3A, dashed line), however its reduction product. IB (FIG. 3A, solid line), exhibits an intense fluorescence spectrum which significantly overlaps neither that of typical proteins nor that of NADH. In contrast to substrate IA, the aldehyde substrate IIA is one of the most intensely fluorescent aldehydes known (FIG. 3B, dashed line). The corresponding alcohol product, IIB (FIG. 3B, solid line). also fluoresces strongly, but at a wavelength well separated from that of IIA. Importantly, as shown in FIG. 4, both IA and IIA substrates and IB and IIB products can be excited effectively and selectively with respect to proteins at $\lambda > 315$ nm.

FIGS. 3A and 3B show that the strong conjugation of the aldehyde carbonyl group with the aromatic ring system of the naphthaldehydes is absent in the corresponding alcohols, and, thus, pronounced spectral changes are observed during their ADH catalyzed redox interconversions. In particular, the reduction of substrate IA to product IB catalyzed by ADH can be monitored by the increase of the alcohol fluorescence In the reduction of the substrate IIA to product IIB catalyzed by ADH. either substrate IIA or product IIB fluorescence can be used to follow the reaction. Because of high fluorescence yields and favorable kinetic properties, activity assays based on these reactions are more sensitive than those based on NADH absorbance or fluorescence.

The present invention provides a quick and accurate simultaneous evaluation of Class I and Class II ADH activities in serum or other body fluids or tissues using a two-assay procedure. One assay uses IA as substrate and the other assay uses IIA as substrate in the presence of the ADH Class I inhibitor 4-methylpyrazole (4-MeP) (Example 2). The two-assay procedure measures the activity of nearly all isozymes of Class I and Class II ADH with the exception of the $\beta\beta$ isozyme forms of Class I ADH. The $\beta\beta$ Class I isozymes have kinetic characteristics quite distinct from other Class I isozymes. To determine the activity arising from the $\beta\beta$ forms of ADH, the four-assay procedure (Example 4) must be used. However, the four-assay procedure only provides estimates of Class I $\beta_1\beta_1$ and/or $\beta_2\beta_2$ isozyme activities. Based on their $k_{cat}$ values the detection limit of these isozymes is estimated to be about 3 nM (Table IV) i.e., considerably lower than that for the other isozymes and, hence, only in instances where the $\beta$ forms greatly exceed the other Class I or II isozymes would their contribution to the rates be significant. This has not been observed in any serum tested thus far.

Figure 10A:
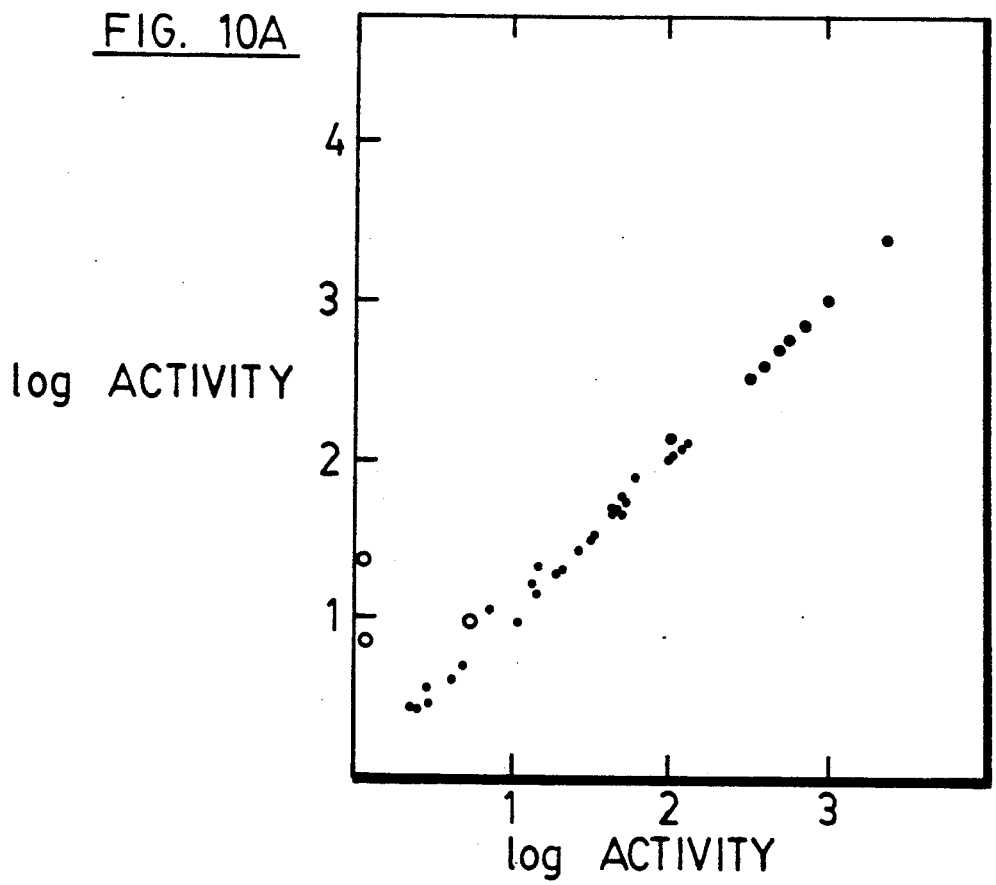
FIG. 10A and 10B are graphs showing the correlation between the Class I (FIG. 10A) and Class II (FIG. 10B) ADH activities obtained by the four-assay procedure (abscissa) as compared with those obtained by the two-assay procedure (ordinate) for Class I (FIG. 10A) and Class II (FIG. 10B) ADH activities (nM/min).
Figure 10B:
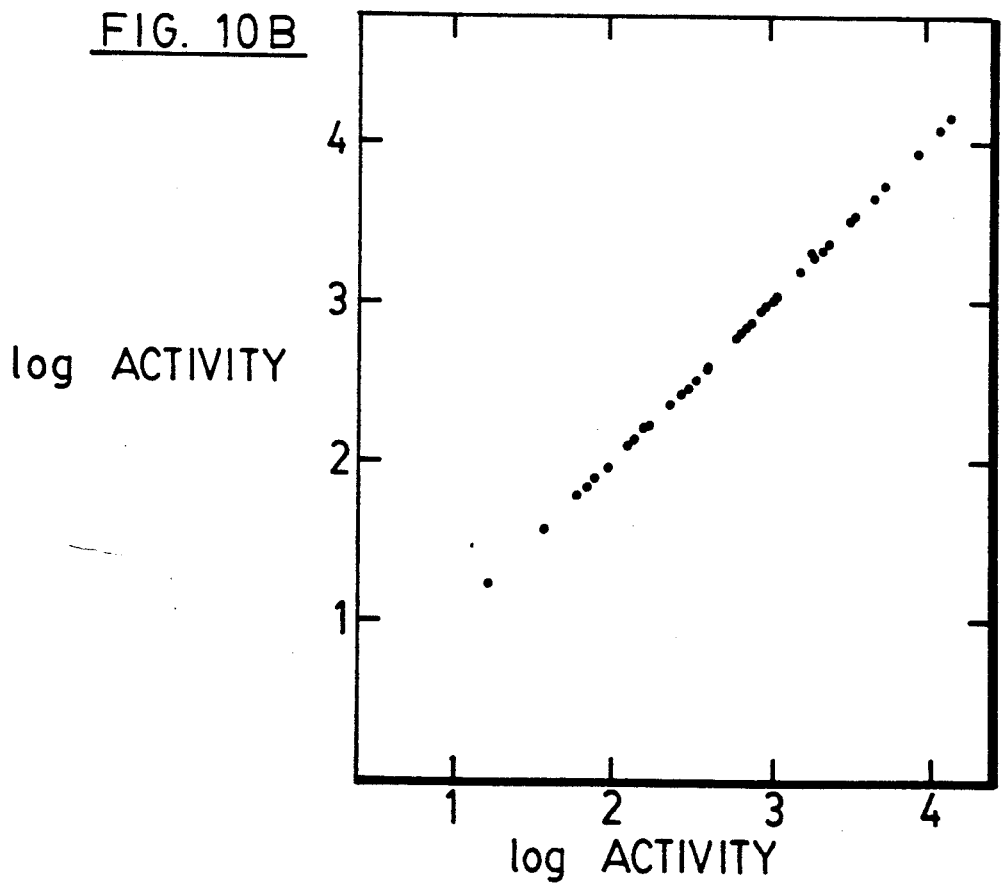

The four-assay procedure (Example 4) is more precise than the two-assay procedure (Example 2) in that it corrects for (a) the overlap in specificity of the substrates, (b) the relative sensitivity of the two classes to 4-MeP inhibition, and, (c) the presence of $\beta\beta$ forms of ADH. by means of a set of simultaneous equations which are easily solved However, for nearly all samples, the much faster and easier two-assay procedure using (1) substrate IA in the absence of any inhibitor, and (2) substrate IIA in the presence of a Class I inhibitor such as 4-MeP is quite satisfactory as shown in Example 5. In Example 5, the validity of the two-assay procedure was analyzed as follows: data obtained by the four-assay procedure were recalculated using the equations for the two-assay method. FIG. 10 shows that the result of such recalculation is valid data in most samples tested. Only in samples where Class II activity is exceptionally high relative to Class I activity (marked in FIG. 10 as open circles) would the two additional rate measurements required by the four-assay procedure be needed to correct resulting discrepancies.

A Class I-selective ADH inhibitor, such as 4-MeP, enhances the specificity of the assay for the Class I and II isozymes with the two substrates about 100 fold due to its highly preferential ability to inhibit Class I relative to Class II ADH (Table IV). In contrast, the inhibitor 4-pentylpyrazole (4-PeP) inhibits both Class I and Class II ADH. For example, using substrate IA, Class I activity is inhibited by greater than 99% with 4-PeP and using substrate IIA, Class II activity is inhibited by more than 90%.

The present invention employs inhibitors such as 4-MeP which are highly selective for a specific class of ADH isozymes thus enabling more exact measurement of the activity of isozyme classes. Similarly, the present invention employs substrates such as IA having high selectivity toward a specific isozyme class further enabling more exact determinations of the ADH activity.

Substrates selective or specific for Class III ($\chi$) ADH would allow for sensitive measurement of that isozyme class Substrate IIA. for example, is a very poor substrate for Class III ADH. With a high Km value of $>0.5$ mM, substrate IIA is completely insensitive for Class III ADH. Because Class III ADH has greater hydrophobic selectivity than Classes I and II ADH, naphthaldehydes and quinoline aldehydes which have aliphatic side chains may provide adequate sensitivity for measuring the amount of Class III ADH in serum. In addition because of its greater hydrophobic selectivity, inhibitor compounds such as 4-alkylpyrazoles having aliphatic side chains of 5 carbons (e.g., 4-PeP) or greater may provide, under certain conditions and at certain concentrations, adequate selectivity for measuring Class III ADH in the presence of Classes I and II. For example, at pH 10 in 0.1M glycine buffer, 1 mM 4-PeP inhibits the activity of Class I and II isozymes $>99.99\%$, but inhibits the activity of Class III only 60%. At 100 $\mu$M 4-PeP, the values for inhibition are: Classes I and II, $>90\%$; Class III $<10\%$. Thus, under certain conditions 4-PeP is clearly useful as a selective inhibitor of Class I and II activities, leaving $>90\%$ of Class III activity intact and measurable.

The improved procedure for purification of Class III ($\chi$) described herein allows highly pure isozyme to be obtained in only 3 to 4 days, a significant advantage in view of its lability (Wagner et al 1984 supra). The purified Class III enzyme, when stored in liquid nitrogen is stable for at least one year without loss in specific activity. The primary improvement in the purification procedure described in Example 1 is the use of HPLC in the final step which provides Class III ($\chi$) ADH as the major active fraction appearing as a single homogeneous peak at 14.5 minutes from the HPLC column. Starch gel and SDS-polyacrylamide gel electrophoresis have confirmed that Class III ADH has been obtained in highly homogeneous form. In addition a more reliable assay for measuring Class III activity throughout the purification is described. A second minor peak with Class III activity was also resolved by the purification with HPLC. which peak appears to correspond to a second minor form of the Class III enzyme known as ($\chi_2$-ADH).

The enhanced specificity and sensitivity of preferred embodiments of the present invention arise in large part from the monitoring of the highly ADH specific formation of the product alcohols IB and IIB. In particular, using methods of the present invention, there is no substrate or coenzyme background rate that requires correction. Such corrections are required with conventional methods of determining ADH activity that are of ADH activity based on nonspecific consumption or production of NADH. Methods of the present invention are from one to two orders of magnitude more sensitive than those using NDMA as substrate or other conventional assays of ADH activity based on NADH absorption. A very simple arrangement suitable for routine measurements, i.e., a conventional fluorometer having standard 4 ml cuvettes and rectangular beam observation, has been employed in methods of the present invention. However, these methods may be further optimized by utilizing a scanning double monochromator such as a Shimadzu model RF5000U spectrofluorometer. With experiments using such a spectrofluorometer, the results of the methods of the present invention were obtained with a 20-fold increase in sensitivity and a 60-fold increase in speed. Methods of the present invention permit for the first time the differential measurement of Class I and Class II ADH activity. From such measurements, it appears that Class II ($\eta$) ADH is the principal form of human ADH in both normal and pathological sera. Therefore, Class II ADH. in particular, appears to be an important genetic and/or biochemical marker for ADH. Because the present invention permits the detection and measurement of such a useful marker, methods of the present invention provide assays useful for the detection of altered alcohol sensitivity or tolerance and alcohol consumption. The present invention therefore also comprehends diagnostic test kits.

This invention is illustrated further by the following examples which are not to be construed as limiting the invention in scope or spirit to the specific procedures described in them.

EXAMPLE 1

Assay Materials, Methods and Conditions

1. Preparation of Purified ADH Isozymes (a) Class I ADH

Human livers were obtained at autopsy within 12 hours postmortem and were stored at −70° C. Individual Class I ADH isozymes were purified from human livers by DEAE-cellulose and CapGapp (4-[4-(N-6-aminocaproyl)aminopropyl]pyrazole-Sepharose) affinity chromatography, as previously described by Wagner et al., 1983, Biochemistry, 22: 1857–1863, with the following modifications. After formation of the Cap-Gapp:$NAD^{30}$:ADH ternary complex, excess $NAD^+$ was removed from the CapGapp affinity resin (U.S. Pat. No. 4,131,727) by washing with two column volumes of 50 mM sodium phosphate, 0.1 mM dithiothreitol (DTT) pH 7.5 in order to minimize production of acetaldehyde and NADH upon subsequent application of the 0.5M ethanol elution buffer. The bulk Class I ADH from the CapGapp column was pooled and concentrated to about 0.1–0.2 liters in ultrafiltration units fitted with PM30 membranes (Amicon, Danvers, Mass.) and then dialyzed overnight against 10 mM sodium phosphate, 0.1 mM DTT, pH 7.4, 2×12 liters. The dialysate was clarified by centrifugation at 17.000 ×g for 20 minutes and added batchwise to a slurry of Affi-Gel Blue (AGB) affinity resin (BioRad, Richmond, Calif.) previously equilibrated with the phosphate buffer in a ratio of 2 ml settled resin per mg protein. The ADH/AGB slurry was incubated at room temperature for two hours, poured into a column, and washed with phosphate buffer. Fractions were monitored for NADH absorbance at 260 nm until the $A_{260}$ of the eluate was <0.01. The ADH was then eluted stepwise with 1M NaCl in the equilibration buffer. Active fractions were pooled and prepared for high pressure liquid chromatography (HPLC) analysis by overnight dialysis against 2 mM sodium phosphate, 0.1 mM DTT, pH 7.4, 2×12 liters, and subsequently concentrated to <10 ml as described above or in Centricon 30 microconcentrators (Amicon, Danvers, Mass.).

The HPLC purification of Class I ADH was performed with a Waters gradient chromatographic system (Waters, Milford, MA) consisting of two M45 pumps, U6K injector with a 2 or 10 ml injection loop, Model 482 variable wavelength UV/VIS detector, Model 680 automated gradient controller, and 740 data module. Analyses of less than 10 mg total protein were carried out at room temperature on an analytical Waters Protein-Pak SP 5PW cation-exchange column (0.75×7.5 cm) (Waters, Milford, Mass.) at a flow rate of 1.0 ml/minute and for protein loads of greater than 10 mg on a semi-preparative scale version of the same column (2.15 x 15 cm) at 3.0 ml/minute. As much as 150 mg ADH were injected onto the semi-preparative column without an overloading problem. The ADH samples (1–10 ml) were loaded onto a column previously equilibrated with 5 mM HEPES (4-(2-hydroxyethyl)-1-piperazine ethanesulfonic acid), 0.1 mM DTT. pH 7.7. Since a constituent of the HEPES buffer was found to adsorb onto the SP 5PW column necessitating frequent and time-consuming regeneration by repeated injection of 1 ml 0.2 N NaOH followed by re-equilibration, sodium phosphate buffer was substituted. The substitution of 2 mM sodium phosphate was found to have no effect on the chromatographic behavior of the isozymes when compared to their behavior in 5 mM HEPES.

Figure 1B:
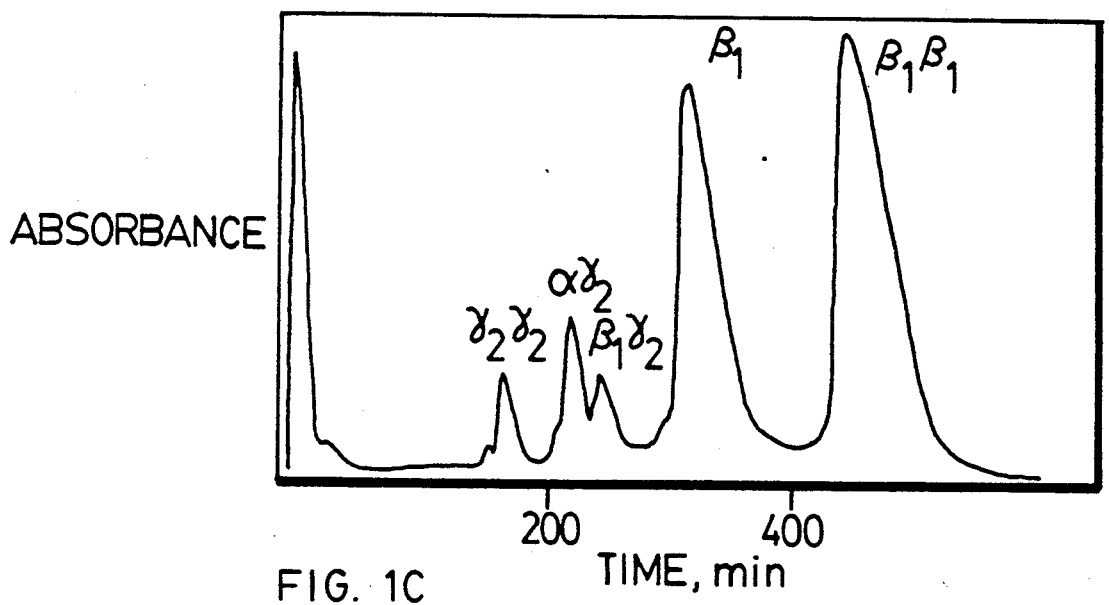
Figure 1C:
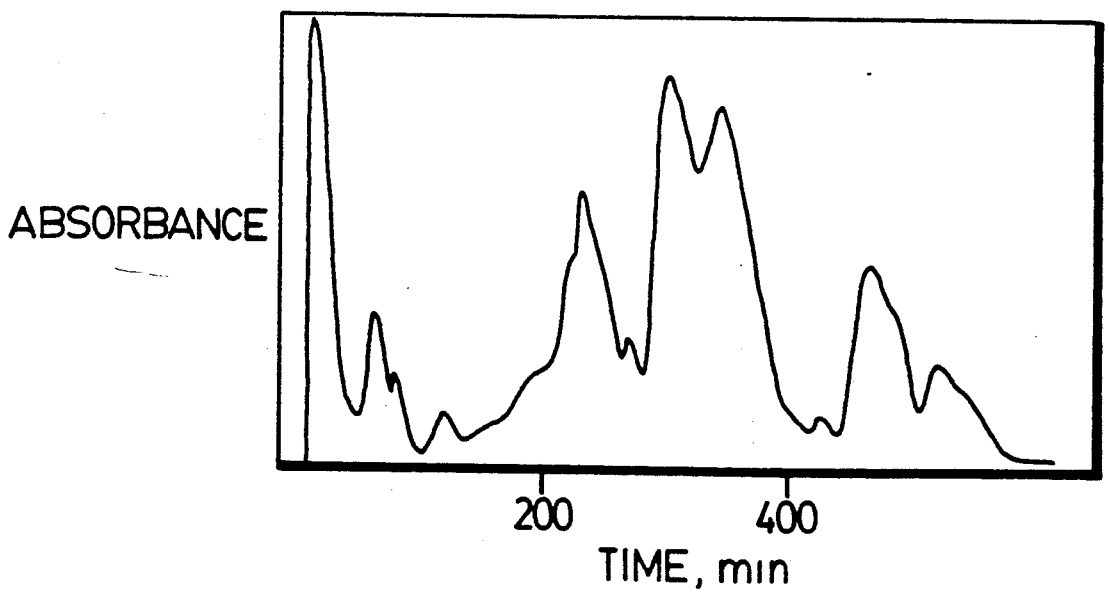

Elution was affected with a linear NaCl gradient, 0–35 mM in the equilibration buffer, over 100 minutes for analytical and 650 minutes for semi-preparative analyses. Peaks were detected by absorbance at 280 nm. Typical HPLC chromatograms for the Class I ADH liver isozymes (a mixture of α, β, γ homodimers and heterodimers) from three different individuals, each containing a different set of ADH isozymes are presented in FIG. 1A–C. FIG. 1A shows ADH of α, $β_1$, $γ_1$ phenotype; FIG. 1B shows ADH of α, $β_1$, $γ_2$ phenotype; and FIG. 1C shows ADH of α, $β_1$, $β_2$, $γ_1$, $γ_2$ phenotype from semi-preparative SP 5PW HPLC analysis. The retention times of the $αβ_1$ and $β_1β_1$ isozymes in FIG. 1A are longer than those of the same isozymes in FIG. 1B due to a slightly shallower gradient employed: 5 to 30 mM NaCl in 10 hours rather than the normal gradient of 5 to 35 mM NaCl in the same time period.

Figure 2A:
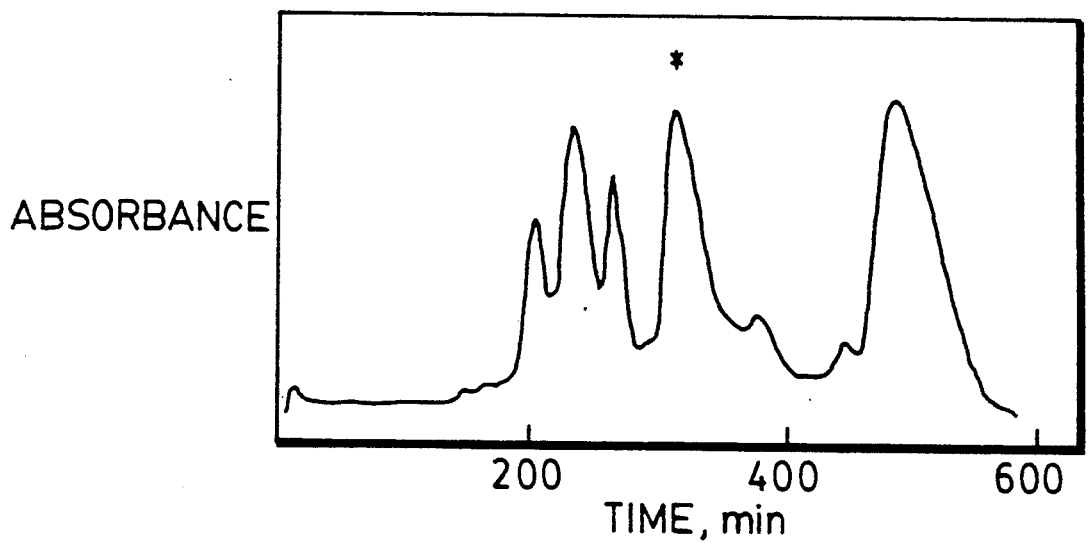
FIG. 2A and 2B are HPLC chromatographs showing the resolution and purification of Class I $\beta_1\gamma_1$ ADH from an individual heterozygous for ADH gene loci. Fractions from the peak marked with an asterisk in FIG. 2A were pooled, concentrated and rechromatographed using a different gradient in FIG. 2B to yield homogenous isozyme.
Figure 2B:
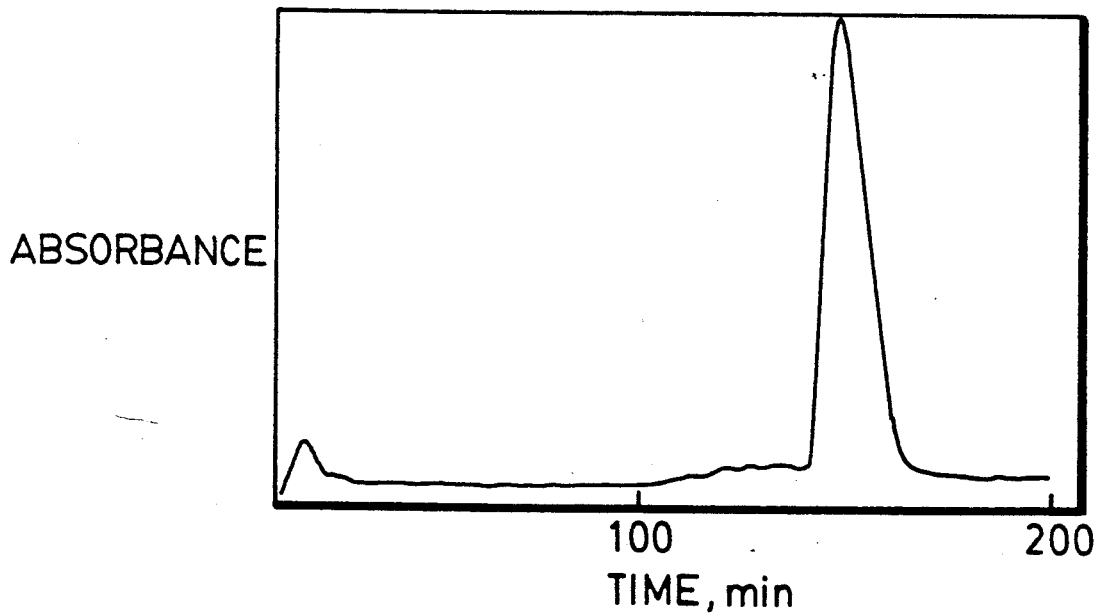

FIGS. 1A and 1B illustrate the resolution of the individual isozymes that is achieved from livers in which a single allelic variant is present, i.e. $γ_1$ or $γ_2$. However, in the case of bulk Class I ADH purified from livers containing two allelic variants, i.e. $γ_1$ and $γ_2$ or $β_1$ and $β_2$, resolution of all isozymes is not readily achieved due to the increased number of heterodimeric isozymes of intermediate chromatographic characteristics. If two allelic variants for both the β and γ subunit types are all present simultaneously ($γ_1$, $γ_2$, $β_1$, and $β_2$) as in FIG. 1C, then resolution of a single, homogeneous isozyme is made even more unlikely. In such cases however, re-chromatography of partially resolved isozymes on HPLC with shallower NaCl gradients has been employed to reduce cross-contamination of isozymes and to obtain purified isozyme forms as shown in FIG. 2. FIG. 2A is an HPLC chromatograph of ADH from an individual heterozygous for ADH gene loci The peak labeled with an asterisk in FIG. 2A was pooled, concentrated and rechromatographed via HPLC as shown in FIG. 2B using a shallower NaCl gradient (5 to 23 mM) to give homogeneous $β_1γ_1$ isozyme.

The purity of each isozyme was evaluated by specific activity, SDS-polyacrylamide gel (Laemmli, et al., 1973, J. Mol. Biol., 80:575–99) and/or urea-polyacrylamide gel (Keung et al., 1985 Anal. Biochem 151:92–96), and starch gel (Bosron et al., 1979, Biochemistry, 18:1101–1105) electrophoresis. Control of column pH and conductivity is critical to maximize reproducibility. The purified Class I isozymes were concentrated to approximately 1 mg/ml and stored in liquid nitrogen at −196° C. Under these conditions, the purified isozymes were found to remain fully active even upon repeated freezing and thawing.

The isozymes used as primary standards were homogeneous based on SDS-polyacrylamide, urea-polyacrylamide and starch gel electrophoresis as described above. They exhibit single symmetrical elution profiles by HPLC ion exchange chromatography, and their specific activity was constant and reproducible. Using ethanol as substrate in a conventional ADH assay as described in part 8 of this Example, the specific activity of each purified ADH isozyme was established by monitoring NADH production by the change in absorbance at 340 nm on a Cary 219 spectrophotometer calibrated with potassium chromate absorbance standards (Fisher Chem. Co., Medford, MA) The activity of the purified ADH Class I isozymes were also assayed according to methods of the present invention (Examples 1 (part 8), 2 and 4).

(b) Class II (η) ADH

A modification of the procedure of Ditlow et al., 1984, Biochemistry 23:6363–68, was used to purify Class II ADH from human livers proceeding from the preparation of Class I isozymes as described in subpart (a) above. The effluent of the CapGapp column obtained during the loading and binding of Class I was concentrated to about 200 ml in an Amicon concentrator with a PM.30 membrane and dialyzed 16 hours against 10 liters of 10 mM potassium phosphate, 0.1 mM DTT, pH 7.4 containing 10 μM octanal. The sample was applied to a column (3×5 cm) of agarose-AMP affinity resin at a flow rate of 0.5 ml/minute followed by washing of the column with 200 ml of the dialysis buffer. The bound enzyme was eluted with 150 ml of the dialysis buffer with a gradient of NADH from 0 to 66 μg/ml. Active fractions measured by the standard Class II assay method (Ditlow et al , 1984, supra were pooled, concentrated as above to 10 ml and dialyzed against 2 mM potassium phosphate, pH 7.4 containing 0.1 mM DTT. The sample was then chromatographed by HPLC using an analytical Waters SP 5PW cation exchange column and the same equipment as for the HPLC purification of Class I (see subpart (a) above) at 1 ml/minute using a linear gradient of 0 to 50 mM NaCl developed in 60 minutes in the above indicated phosphate buffer. The homogeneous Class II ADH eluted at 30 minutes as a single homogeneous peak of absorbance at 280 nm and showed a single band on starch gel electrophoresis with a specific activity of 1.5 U/ml.

(c) Class III (χ) ADH

Adult human livers were obtained at autopsy and stored at $-70°$ C. Class III (χ) ADH as isolated by modification of the procedure of Wagner et al., 1984, Biochemistry 23:2193 as follows. Unless otherwise stated, all purification steps were done at 4° C. Throughout the purification, Class III ADH activity was measured using 0.5 mM ω-hydroxydodecanoic acid as substrate in 0.1M glycine-NaOH buffer, pH 10.0, 20 mM NaCl, 2.5 mM $NAD^+$ and 2 mM 4-MeP. The presence of the large amount of inhibitor allows the detection of Class III ADH activity in mixtures containing various amounts of other ADH isozymes. Although more time-consuming, this assay proved more reliable at all stages of the purification scheme than the conventional assays using 0.5M ethanol as substrate (Wagner et al., 1984, supra).

Human liver (100 g) was cut into pieces (approximately 4×4 cm) and thawed in 100 ml of distilled water containing 1 mM sodium ascorbate. The tissue was ground in a Waring blender and then homogenized in a Polytron (Brinkmann Instruments, Westbury, N.Y.) instrument. The homogenate was centrifuged immediately for 45 minutes at 20,000 ×g. The supernatant was dialyzed overnight against 15 liters of 10 mM Tris-HCl buffer, pH 7.9, containing 1 mM sodium ascorbate.

The dialyzed homogenate was then passed through 500 ml of DEAE cellulose (DE.52, Whatman International Ltd., Maidstone, England) equilibrated with 10 mM Tris-HCl buffer, pH 7.9, containing 1 mM sodium ascorbate. Class I and II isozymes were washed from the resin packed in a sintered glass funnel. The bound χ-ADH was then eluted with 5000 ml of 0.1M Tris-HCl, 0.5M NaCl containing 1 mM ascorbate, pH 8.0. Octanal, from a 10 mM solution in methanol, was added to the pooled eluate to a concentration of 10 μM and the fraction concentrated to about 100 ml with an Amicon concentrator (Denvers, Mass.) equipped with a PM 30 membrane. The concentrated enzyme solution was dialyzed against 15 liters of 50 mM potassium phosphate buffer, pH 7 4, 0 1 mM DTT.

The dialyzed solution was clarified by centrifugation for 20 minutes at 20,000 X g and loaded onto a 1.5 x 5 cm column of agarose hexane adenosine 5' phosphate (AGAMP) affinity resin type 2 (P-L Biochemicals, Milwaukee, Wis.) equilibrated with 10 mM potassium phosphate buffer, pH 7.4, at a flow rate of approximately 1 column volume per hour. The column was then washed extensively with the equilibration buffer and developed with a total of 200 ml of a 0–25 μM NADH linear gradient prepared in 10 mM potassium phosphate, pH 7.4. The active fractions eluted at 2–3 μM NADH and were pooled and concentrated by use of Amicon concentrator with a PM 30 membrane, after making the solution 10 μM in octanal. The enzyme solution was repeatedly concentrated and diluted with 10 mM Tris-HCl, pH 8 0, until no NADH absorbance at 340 nm remained in the effluent (usually after 5 ×1:10 dilutions).

The final purification step was performed at ambient temperature with a DEAE 5PW (Waters Milford. MA) anion exchange HPLC column (7.5 cm×7.5 mm) equilibrated with 10 mM Tris-HCl 1 mM DTT pH 8 0 and eluted with a NaCl gradient using the same equipment as for the HPLC purification of Class I (see subpart (a) above). The column was developed at a flow rate of 1 ml/minute with a NaCl gradient with linear segments in the same buffer with the following program: Time (minutes), (NaCl)(mM); 0, 0., 5, 20; 12, 24, 15, 40., 20, 40; 25, 200. The absorbance at 280 nm was monitored, and generally 0.5 ml fractions were collected and assayed for activity as described above.

About 80% of the activity was recovered in a major homogeneous peak with a retention time of 14.5 minutes. A minor peak appearing at 21.3 minutes corresponds to a minor form of Class III ADH ($\chi_2$-ADH) that migrates on starch gel electrophoresis more anodically than the major Class III (χ-ADH) enzyme (Pares and Vallee. 1981, Biochem. Biophys. Res. Comm. 98:122; Vallee and Bazzone, 1983, Curr. Topics Biol Med. Res. 8:219; Adinolfi at al., 1984, Ann. Hum. Genet. 48:1). The active fractions of Class III (χ) and Class III ($\chi_2$) were separately concentrated with Centricon 30 microconcentrators (Amicon) and kept as beads in liquid nitrogen. This improved procedure was also used to isolate horse χ-ADH (Dafeldecker and Vallee, 1982, J. Prot. Chem. 1:59). It eluted from the HPLC column 7 minutes later than the human Class III (χ) ADH under identical conditions.

2. Preparation of Preferred Substrates and Products

Presently preferred ADH substrates and products and their preparation are as described in Wierzchowski et al., 1989, Anal. Biochem. 178:57–62 and briefly described below.

(a) Substrates 4-methoxy-1-naphthaldehyde (substrate IA) was purchased from Aldrich Chemical Co. (Milwaukee, Wis.) and was recrystallized twice from ether-hexanes (mp 34° C.). It exhibited a single spot on TLC (Silica-Gel 60 F254, Merck, FRG, with methylene chloride-hexanes as solvent) and fluorometric spectral analysis showed the compound to be free of any traces of fluorescent impurities.

6-methoxy-2-naphthaldehyde (substrate IIA) was synthesized from 6-methoxy-2-carbethoxynaphthalene, prepared from 6-methoxy-2-naphthonitrile, ethyl 2-bromoisobutyrate, and zinc dust as described by Horeau et al., 1947, Bull. Soc. Chim. Fr. 14:53–59. The keto-ester intermediate, mp 74°–76° C. (lit. 72.5–73.5° C.) was reduced to the corresponding secondary alcohol ester with sodium borohydride in ethanol at 4° C. and then thermally decomposed (Horeau et al. 1953, Compt. Rend. 236:826–8) to afford the final compound. The aldehyde was 25 purified either by zone sublimation or via the bisulfite adduct; mp 80°–81.5° C.; (lit. 79° C. Horeau et al., 1953, supra: lit. 81°–82° C. Gandhi et al., 1955 J. Chem. Soc., 2530).

Both methoxynaphthaldehydes (IA and IIA) are stable in the crystalline state, and spectral changes were not observed when they were stored at 20° C. for 30 days in water:acetonitrile (70:30 v/v) stock solutions. However, dilute aqueous solutions are much less stable and TM >were therefore prepared daily. The dilute solutions (300 μM) were prepared by diluting 1 ml of the stock solution to 10 ml with water.

(b) Products

Reduction of substrate IA with sodium borohydride provided 4-methoxy-1-naphthalenemethanol (product IB). One gram of IA was dissolved in an aqueous acetonitrile solution containing 0.1M phosphate, pH 5. An aqueous solution of sodium borohydride was added dropwise with stirring until the absorption at 336 nm disappeared. The pH of the reaction mixture did not exceed 10.0. The product was extracted with ether and recrystallized from ether-hexanes to give almost colorless needles, mp 75°–76° C. (lit. 76° C. Schreiber et al., 1962, J. Am. Chem. Soc. 84:859–63). This product was spectrally and chromatographically (by thin layer chromatography) identical with the product of the enzymatic reduction of 4-methoxy-1-naphthaldehyde by ADH.

Reduction of 6-methoxy-2-naphthaldehyde (IIA) with sodium borohydride in ethanol at 4° C. yielded 6-methoxy-2-naphthalenemethanol (product IIB), mp 122° C. (lit. 116°–117° C.).

Solutions of the products IB and IIB (200–400 μM) are stable for up to a week and were made by dissolution in absolute ethanol followed by dilution in water to a final ethanol content of <5%. Concentrations were determined spectrophotometrically using a molar absorptivity of 5700 $M^{-1} cm^{-1}$ at 296 nm for IB and 1270 $M^{-1} cm^{-1}$ at 330 nm for IIB.

3. Preparation of Inhibitors (a) 4-methylpyrazole

4-Methylpyrazole (4-MeP) was purchased from Aldrich (Milwaukee, Wis.). Stock solutions of 4-MeP (12 mM) were prepared in water.

(b) 4-Pentylpyrazole

4-Pentylpyrazole (4-PeP) was prepared by adding 2-Pentyl-1,1,3,3-tetraethoxypropane dropwise with stirring to a solution having a molar equivalent of hydrazine sulfate in 6M HCl at 40°–45° C. The mixture was kept at this temperature for 1 hour and the temperature then raised to 90° C. for 30 minutes. After the mixture cooled, 40% w/w 30 NaOH was added and the mixture thoroughly extracted with ether. Drying the ether solution over $MgSO_4$ afforded 4-PeP. Stock solutions of 4-PeP (3 mM) were prepared by dissolution first in acetonitrile, followed by dilution with water to a final acetonitrile concentration of 8%.

4. Sample Storage

Fresh serum samples were obtained from the Clinical Chemistry Laboratory at Brigham and Women's Hospital, Boston, Mass. All serum measurements reported herein were performed within 5 hours of phlebotomy unless otherwise indicated On storage there is considerable variation in the ADH activity of serum samples from the same and different patients. FIGS. 5A and 5B show the effect of storage at 4° C. (closed circles) and room temperature (closed squares) in a typical serum sample, using substrate IA (FIG. 5A) and substrate IIA (FIG. 5B) as measured by the four-assay procedure of Example 4. The loss of activity is first order when sera are stored at room temperature as shown in FIG. 5 with half-lives from a few hours to >3 days for both Class I and Class II ADH. Storage at 4° C. provides some improvement in stability but storage of samples at −70° C. stabilizes both Class I and Class II activities for at least one month as shown in Table II.

TABLE II

Effect of Storage Conditions and Time on ADH Activity in Serum

| ADH Class[a] | Storage Temperature (°C.) | Storage Time (days) | Average Activity Retained (%) | n | Coefficient of variation (%) |
|---|---|---|---|---|---|
| I | 23 | 1 | 58 | 7 | |
| II | 23 | 1 | 66 | 7 | |
| I | 23 | 2 | 34 | 11 | 54 |
| II | 23 | 2 | 51 | 11 | 29 |
| I | 4 | 2 | 73 | 21 | 30 |
| II | 4 | 2 | 55 | 21 | 47 |
| I | −70 | 30 | 91 | 10 | 19 |
| II | −70 | 30 | 100 | 10 | 13 |

[a]Determined by the 4-assay procedure described in Example 4.

5. Other Materials

Crystalline horse ADH was purchased from Boehringer-Mannheim (Indianapolis, Ind.). $NAD^+$ and NADH, both grade III, were obtained as preweighed samples from Sigma Chemical Co. (St. Louis, Mo.); isobutyramide was from Aldrich., ethanol (100%) was from U.S. Industrial Chemicals Co. (New York, N.Y.); Mes acid (2-(N-morpholino)ethanesulfonic acid) was recrystallized from water. All other reagents were of analytical grade. Deionized, glass-distilled water was used throughout.

A 1 mM solution of NADH was prepared daily for use in assays by dissolving a preweighed sample in the serum assay buffer 0.1M sodium phosphate pH 7.6, 25° C.

6. Spectral Measurements

Ultraviolet absorption spectra were measured on a Cary 219 or Hewlett-Packard 8451 spectrophotometer. Fluorescence measurements were made in a Perkin Elmer MPF3 spectrofluorometer, equipped with an Osram XBO 150 Watt Xenon lamp, an R446 photomultiplier, and thermostatted cell holder through which water was passed from a Poly-Temp circulator with the following spectrometer settings: excitation wavelength 316 nm. bandwidth 8 nm for both substrate IA and IIA; emission wavelength. 370 nm for substrate IA and 360 nm for substrate IIA, emission bandwidth 24 nm. Changes in fluorescence as a result of oxidation or reduction of the substrate was then measured in the ratio mode. Generally, for fluorometric reactions (see part 8 below). a sensitivity setting of 3 was used with compensation of fluorescence background by the zero suppression control of the instrument.

7. Spectrophotometric Procedure (a) Standard Assay for Ethanol Oxidation

Standard assays for ethanol oxidation activity (Dalziel, 1957, Acta Chem Scand 11:1706-23) were carried out on a Cary 219 spectrophotometer interfaced with an Apple IIe microcomputer, using software provided by Varian Associates. The reaction mixture contained 2.5 mM NAD+ in 0.1M glycine-NaOH buffer. pH 10.0, and 33 mM or 0.2M ethanol for Class I and Class II ADH, respectively.

Aldehyde reduction was monitored by following the decrease of absorption at 340 nm in 40 mM Mes buffer, pH 7.1. in the presence of saturating NADH, 50 $\mu$M for Class I and 100 $\mu$M for Class II. Both NADH and the aldehydes exhibit absorption at this wavelength and the total decrease of molar absorptivity was determined to be $1.8 \times 10^4 M^{-1} cm^{-1}$ for the IA/NADS and $1.27 \times 10^4 M^{-1} cm^{-1}$ for the IIA/NADH system. Initial reaction rates were measured and kinetic parameters determined by conventional procedures as described by Segel, 1975, Enzyme Kinetics, pp. 591-597, Wiley, N.Y.

(b) Standard Assay for NDMA Reduction

The p-nitrosodimethylaniline (NDMA) reduction assay of Shursky et al., 1979, Anal. Biochem. 99:65-71, was modified and automated as follows. A 5 mg sample of NADH was dissolved in 65 ml of 0.125M sodium phosphate at pH 7.0, 162 $\mu$l of this NADH solution was pipetted into each well of a 96-well microtiter plate To each well was added 12.5 $\mu$l of sample serum and a blank absorbance as then measured at 25° C. on a thermostatted Dynatech MR 600 reader set to measure 440 nm. The reactions were initiated by adding to each well via an eight port auto pipetter 100 $\mu$l of a 10 mM aqueous NDMA solution (1.5 mg dissolved in 100 ml water) diluted 1 to 1 with 0.125 mM pH 7.0 phosphate buffer. Three absorbance readings for each well measured 5 minutes apart were stored in a computer. The reaction rates were calculated by standard regression analysis of the three absorbance readings.

ADH activities determined according to this assay are reported as NDMA units. One NDMA unit is defined as the amount of ADH, which reduces 1 $\mu$mole of NDMA in one minute at 25° C. in the presence of saturating amounts of NADH at pH 7.0.

8. Fluorometric Procedure (a) Fluorometric Reaction

All reaction mixtures (3 ml total volume) were prepared directly in 1 cm pathlength, 4 ml fluorometric cuvettes by adding 150 $\mu$l of the 300 $\mu$M substrate solution (e.g substrate IA or IIA) 100 $\mu$l of the 1 mM NADH solution (prepared as in part 5 above) and 2.69 ml of assay buffer (0.1M phosphate, pH 7.6). After thermal equilibration (25° C.) for 5 minutes, 60 $\mu$l of isozyme sample (either serum or purified ADH isozymes) was added to the cuvette.

The linear increase of fluorescence was then recorded for 1-10 minutes, until 0.03-1 $\mu$M of substrate was consumed. Larger substrate consumption was not found to be desirable (described in subpart (c) below). After this period the instrument sensitivity setting was reduced 10-30 fold, the signal compensated once again by zero suppression (see part 6 above); and 60 $\mu$l of 200-400 $\mu$M product (e.g., product IB or IIB) was added to provide an internal standard. The added product fluorescence intensity was then measured Fluorescence measurements were optimized for samples with low activity ($<$1 nM/minute). For samples with higher activity, repeat measurements were made with the serum volume reduced from 60 $\mu$l to 10 $\mu$l. Rates measured in the presence of the 0.2 mM ADH inhibitors. 4-MeP or 4-PeP, were made by adding 50 $\mu$l of 12 mM inhibitor to the cuvette prior to the assay buffer, and the reaction was carried out as above.

(b) Optimizing Assay Conditions for Serum Assays

Aldehyde reduction and 4-MeP inhibition are near optimal at pH 7.6 which was adopted for the study of serum samples. Phosphate was chosen as the buffer, since it does not react with aldehydes, in contrast to amines which alter the fluorescent properties of the substrates. Under the conditions used and with 15$\mu$M concentrations of either substrate IA or IIA, Table IV below shows that 0.2 mM 4-MeP instantaneously inhibits all Class I isozymes by more than 90%. but Class II ADH by only 11%.

The optimal substrate concentration of about 15 $\mu$M was adopted for both substrates IA and IIA. Because the Michaelis constants of substrates IA and IIA for most of the ADH isozymes are between 1 and 10 $\mu$M (Table III), at the substrate concentration employed, the rates are not at maximal velocity. However, higher concentrations of substrate, which in principle would increase initial velocities, result in increased absorption of the sample and a loss of sensitivity due to inner filter and reabsorption effects; lower substrate concentrations result in the expected decrease in sensitivity. The use of the purified alcohol reaction products as internal standards allows for the measurement of reaction rates in samples with an absorbance as high as 0.3 without correction for the inner filter effect.

Human serum is known to fluoresce over a broad spectral region (Wolfbeis et al., 1985. Anal. Chim. Acta. 167:203-315); the instrumental settings should therefore be chosen to optimize the signal/background noise ratio. Nonetheless, the fluorescence of the alcohol products IB and IIB is quenched significantly when serum is present at concentrations greater than that afforded by a 50-fold dilution. A 50-fold dilution of serum minimizes interference and maximizes sensitivity. At this dilution, alcohol product IB is only quenched 15% while IIB is quenched 5%. In a small number ($<$1%) of serum samples tested, background fluorescence up to 50 times above the normal level was observed which substantially reduced the sensitivity of measurements. The cause of this background fluorescence is unknown (c) Calculation of reaction rates.

The rates of aldehyde reduction, determined as initial velocities (V) and expressed in units of nM/minute, were calculated according to:

$$V = \frac{C_{st}}{F_{st}} \cdot \left( \frac{F_t - F_O}{t} \right) \qquad (1)$$

where the quantity in parentheses is the slope of the linear fluorescence increase calculated from the quantities $F_t$ and $F_O$, the fluorescence at time t and at the beginning of the reaction, respectively. $C_{st}$ is the concentration of the product used as a standard added to the cuvette after the initial rate had been measured and $F_{st}$ is the fluorescence intensity of the added product To maintain optimal fluorescence conditions and low absorbencies in the cuvette the extent of the reactions was limited to <1 μM product formation and to <6 μM product addition in the standardization procedure. With these restrictions, the maximal change of the absorbance of the sample at 326 nm during the procedure is less than 0.05, and, hence corrections for the inner filter effect were not required.

(d) Kinetic Parameters

Table III shows kinetic parameters of the ADH enzymatic reaction using purified Class I, II and III ADH isozymes with substrates IA and IIA, including the $K_m$ and the $k_{cat}$ values of IA and IIA, for eight purified human liver ADH isozymes. Additionally the reaction rates for these isozymes were compared to those measured by the standard assay for ethanol oxidation (see part 7 above) at pH 10.0 the optimum for oxidation of ethanol by ADH. The rate of IA reduction for all Class I isozymes except the $\beta_1\beta_1$ form is 1.5- to 4-fold faster than that of ethanol oxidation as measured by the conventional ethanol oxidation assay. The reduction of IIA by Class I isozymes is generally slower, but still comparable to that of ethanol oxidation in the standard assay. Table III illustrates that IIA is an excellent substrate for Class II ($\eta$) ADH, with a rate of IIA reduction at least 8-fold faster than that of ethanol oxidation.

The $K_m$'s in Table III for substrates IA and IIA range from 0.35 to 20 μM. Most of them, in particular the $K_m$'s of the $\gamma$-containing Class I ADH isozymes, are close to or below 1 μM. In some instances particularly when the conventional assay monitoring NADH or aldehyde absorption proved insufficiently sensitive, the fluorometric assays of the present invention were the only ones to provide accurate $K_m$ values. For example reaction rates as low as 1 nM/min can be measured with a conventional spectrofluorometer using IA as substrate, allowing measurements of purified Class I isozyme in concentrations as low as $10^{-11}$ M.

TABLE III

Kinetic Parameters for Enzymatic Reduction of Methoxynaphthaldehydes Substrates by Various Isozymes of Human ADH[a]

| Substrate | Isozyme | $K_m$ (μM) | $k_{cat}$[b] (min$^{-1}$) | v/v (EtOH)[c] | Method[d] |
|---|---|---|---|---|---|
| IA | $\alpha\beta_1$ | 8.5 | 450 | 1.59 | B |
| | $\alpha\gamma_1$ | 2.8 | 500 | 2.71 | A |
| | $\beta_1\beta_1$ | 4.0 | 2 | 0.08 | B |
| | $\beta_1\gamma_1$ | 0.60 | 265 | 0.93 | A |
| | $\beta_1\gamma_2$ | 1.6 | 290 | 3.4 | A, B |
| | $\gamma_1\gamma_1$ | 2.30 | 610 | 1.54 | A |
| | $\pi$ | 20.0 | 50 | 0.20 | B |
| | $\chi$ | NR[e] | NR | — | A, B |
| | Horse[f] | 33 | 26 | 0.04 | B |
| IIA | $\alpha\beta_1$ | 11.5 | 160 | 0.74 | B |
| | $\alpha\gamma_1$ | 0.58 | 150 | 1.06 | A |
| | $\beta_1\beta_1$ | 5.4 | 77 | 4.85 | B |
| | $\beta_1\gamma_1$ | 0.40 | 170 | 0.53 | A |
| | $\beta_1\gamma_2$ | ~0.8 | ~70 | 1.6 | A |
| | $\gamma_1\gamma_1$ | 0.35 | 110 | 0.45 | A |
| | $\pi$ | 2.6 | 1500 | 8.0 | B |
| | $\chi$ | >500 | —[b] | — | A |
| | Horse[f] | 2.2 | 2150 | 2.5 | B |

[a]Determined at pH 7.0, with 50 μM NADH (see Wierzchowski, et al., 1989, Anal. Biochem. 178: 57-62).
[b]Calculated relative to the active site concentration (see Wierzchowski et al., supra).
[c]Rate of reaction relative to ethanol oxidation at pH 10.0.
[d]Method for determination of $K_m$ and $k_{cat}$: A, fluorometric; B, spectrophotometric. Typical error is 15% and about 20% for $K_m$ and $k_{cat}$ values, respectively.
[e]No reaction detected.
[f]Crystalline horse ADH, containing more than 90% EE isozyme $k_{cat}/K_m = 5 \times 10^4$ min$^{-1}$ M$^{-1}$.

Table IV summarizes kinetic parameters of the ADH enzymatic reaction using purified Class I and II ADH isozymes including the $\beta\beta$ forms, with substrates IA and IB. Tables III and IV show that substrates IA and IIA are highly selective for Class I and Class II ADH, respectively. Excepting $\beta\beta$, IA is a good substrate for all Class I isozymes with $k_{cat}$ values between 265 and 610 min$^{-1}$, a relatively narrow range, while the $k_{cat}$ for the Class II isozyme is only 40 min$^{-1}$. In contrast, IIA is an excellent substrate for Class II ($\eta$) ADH, with a $k_{cat}$ value of 1500 min$^{-1}$, 10-fold higher than for the Class I isozymes. 4-MeP further enhances the specificity of these classes for the two substrates about 100 fold, since it inhibits Class I much more effectively than Class II ADH. While IIA is also a substrate for Class III ($\chi$) ADH, it is a poor one and its high $K_m$ value of >0.5 mM (Table III) thus renders an assay with substrate IIA insensitive for Class III ADH.

TABLE IV

Kinetic Parameters of the ADH Isozyme Classes Used to Calculate Class I and II ADH Activity and Concentrations.

| ADH Class | Substrate | $K_m$ (μM) | $k_{cat}$ (min$^{-1}$) | 4-MeP Inhibition[a] (%) |
|---|---|---|---|---|
| I[b] | IA | 0.6–8.5 | 350[c] | 98 |
| I[b] | IIA | 0.4–11.5 | 110[c] | 92[c] |
| II[b] | IA | 20 | 50 | 11 |
| II[b] | IIA | 2.6 | 1500 | 11 |
| $\beta_1\beta_1$[b] | IA | 4.0 | 2 | ~95 |
| $\beta_1\beta_1$[b] | IIA | 5.4 | 77 | 98 |
| $\beta_2\beta_2$ | IA | nm[e] | <1 | nm[e] |
| $\beta_2\beta_2$ | IIA | nd[d] | 120 | 97 |

[a]Calculated as the ratio of the inhibited rate over the control rate times 100.
[b]Data from Table III and Wierzchowski et al., 1989, Anal. Biochem. 178: 57-62.
[c]Average value for Class I isozymes, except for the $\beta\beta$ forms.
[d]Not determined.
[e]Not measurable.

Figure 7A:
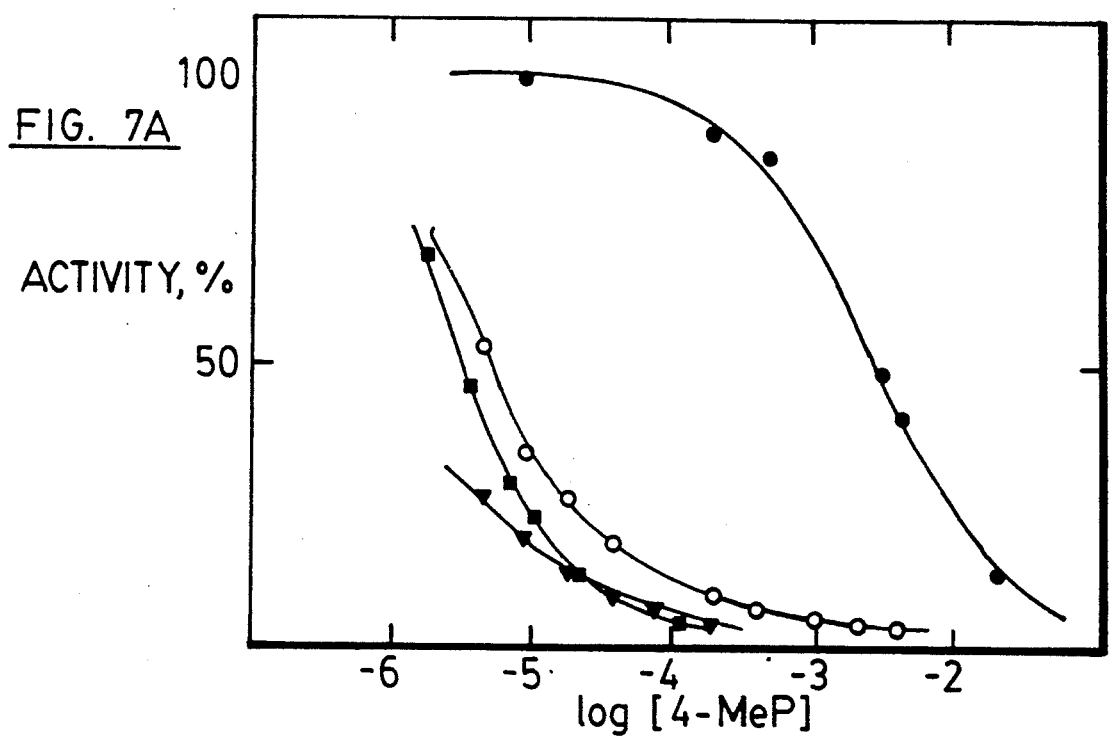
FIG. 7A and 7B are graphs of inhibition profiles for ADH activity in human serum (open circles) as compared to purified human liver ADH isozymes (Class II, closed circles. Class I $\alpha\alpha$, squares; Class I $\beta_1\beta_1$, triangles) with IA (FIG. 7A) and IIA (FIG. 7B) as substrates.
Figure 7B:
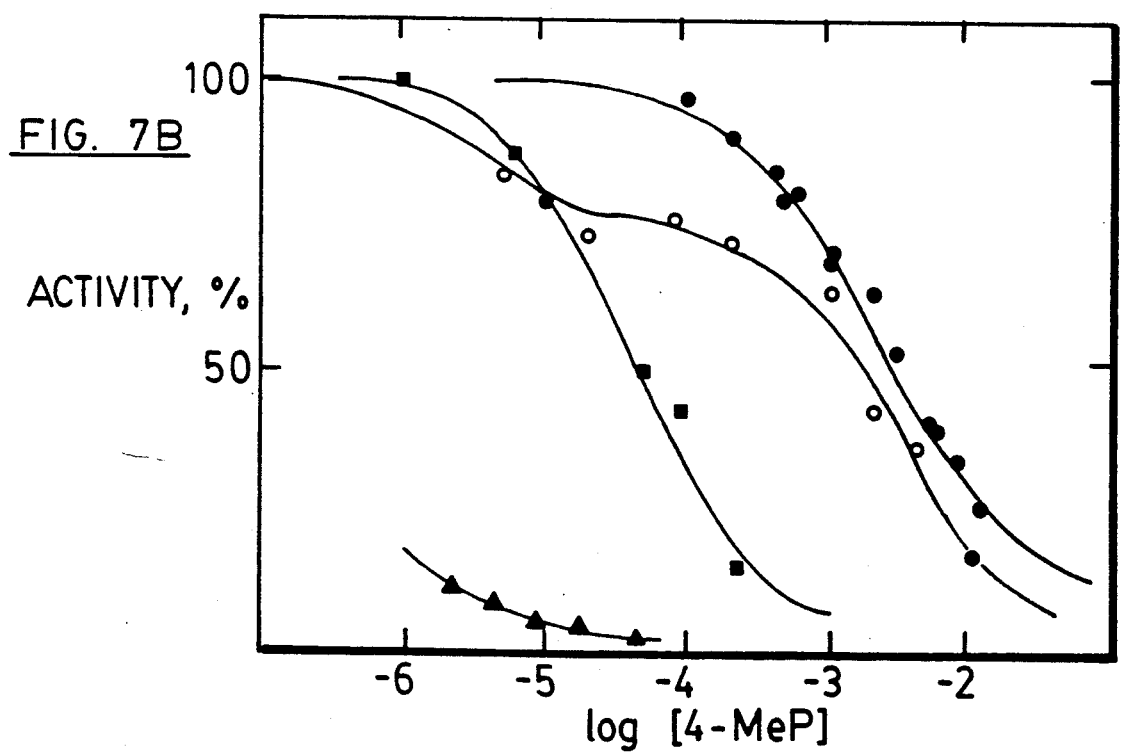

The results of the resolution of purified ADH isozyme activities are shown in FIG. 7 as inhibition profiles. The inhibition profile for ADH activity in human serum (open circles) is compared with that of (i) purified Class II (closed circles), (ii) purified Class I $\alpha\alpha$ (closed squares) and (iii) purified Class I $\beta_1\beta_1$ (closed triangles). The serum sample (open circles) contained ~0.1 μM Class II and ~0.03 μM Class I ADH. The inhibition of serum activity toward IA and IIA as a function of 4-MeP concentration, thus compares well with that obtained for purified Class I and Class II ADH.

Figure 8A:
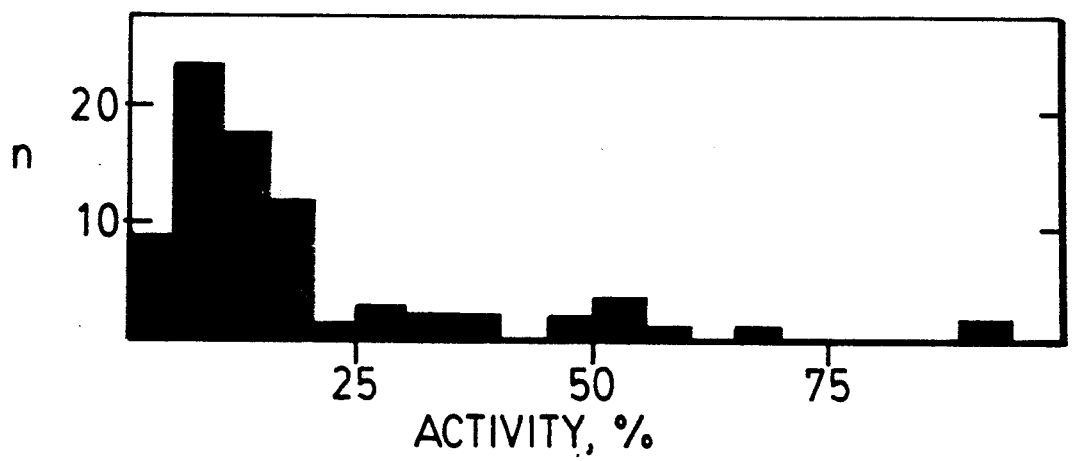
FIG. 8A, 8B and 8C are histograms of the degree of inhibition of ADH catalyzed fluorescent product formation in human sera: of IA by 0.2 mM 4-MeP (FIG. 8A); of IIA by 0.2 mM 4-MeP (FIG. 8B); of IIA by 0.2 mM 4-PeP (FIG. 8C).
Figure 8B:
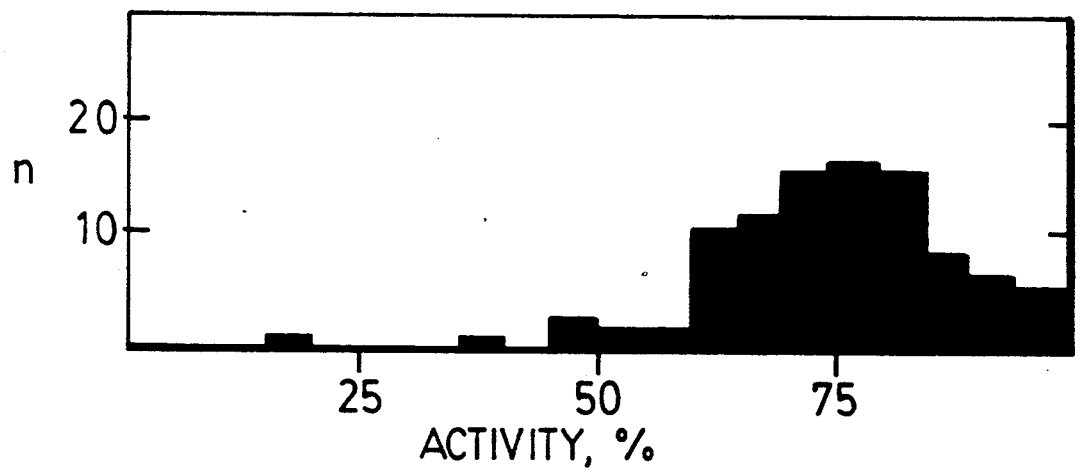
Figure 8C:
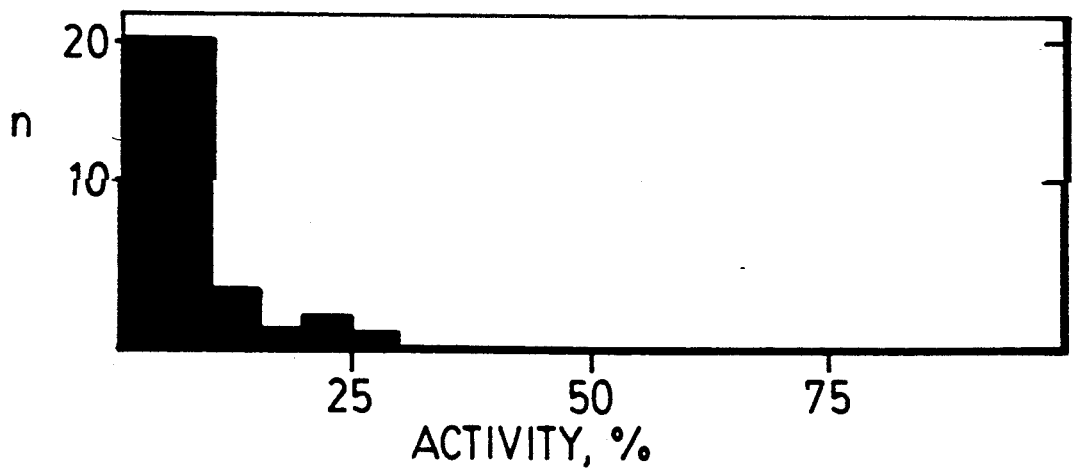

The activities of a large group of serum samples were further examined for inhibition by 4-MeP and 4-PeP, both at 0.2 mM, a concentration that abolishes 95-98% of the Class I and Class II ADH activity as shown in Table IV above. FIG. 8 shows that 4-MeP inhibited more than 90% of the IA activity in the majority of samples (FIG. 8A), but the activity toward IIA remained at 70% or greater (FIG. 8B). In contrast, 4-PeP inhibited activity toward IA by greater than in all cases and IIA by more than 90% in virtually all samples examined (FIG. 8C). The total number of samples examined was 83 for FIG. 8A, 105 for FIG. 8B, and 44 for FIG. 8C.

EXAMPLE 2

Resolution of the Class I and Class II Alcohol Dehydrogenase Isozyme Activities Using Purified ADH Isozymes By the Two-Assay Procedure Class I and Class II isozymes were purified according to the procedures of Example 1. These purified ADH isozymes were utilized as solutions containing 10 μM DTT; the DTT is required to stabilize highly diluted enzyme in the absence of serum. For the simultaneous evaluation of the Class I and Class II ADH activities, two fluorometric assays according to Example 1 were carried out: one with IA as a substrate, $V_1$, and the second with IIA as substrate in the presence of 0.2 mM 4-MeP, $V_4$. Corrections for a non-ideal specificity of the assays for the two isozyme classes are based on the following equations that relate the measured reaction rates, $V_1$ and $V_4$, to the actual activities contributed by the Class I and Class II ADH, AI and AII. respectively:

$$V_1 = A_I + aA_{II} \quad (2)$$

$$V_4 = (1-c)A_{II} + fA_I \quad (3)$$

The constants a, c and f have the following meaning and values:

a is the ratio of specific rates for Class I to Class II ADH with IA as substrate under the assay conditions and is equal to 0.022;

c is a degree of inhibition of Class II ADH by 0.2 mM 4-MeP, with IIA as substrate and equals 0.11;

f is the ratio of the specific rates for Class I to Class II ADH with IIA as substrate (0.27, average value), multiplied by a fraction of Class I activity not inhibited by 0.2 mM 4-MeP (0.08).

The values for these constants were determined with purified Class II ADH or a mixture of purified Class I isozymes, under the fluorometric assay conditions described above in Example 1.

The above calculations for the two-assay procedure neglect the $\beta\beta$ form of ADH. which has kinetic characteristics quite distinct from other Class I isozymes (Tables III and IV above). The four-assay procedure, described in Example 4 below, enables estimation of the $\beta\beta$ ADH activity, albeit with lower sensitivity and accuracy. For all serum samples assayed thus far, the $\beta\beta$ activity was found to be low by the four-assay procedure and, hence, it does not interfere with evaluations of Class I and Class II ADH activities by the two assay methods described in this Example. Unless otherwise indicated, however, the four-assay procedure was used in the results reported herein. Comparison of the four-assay and two-assay procedures in application to serum ADH measurements is given in Example 5.

EXAMPLE 3

Assay of Alcohol Dehydrogenase Activities in Reconstituted Inactive Human Serum Since primary standards or reference sera with known amounts of ADH are not available, purified ADH isozymes (Example 1) were added to assays containing 50-fold diluted. inactive serum to measure the accuracy of the assay. The ADH isozymes employed were electrophoretically homogeneous with symmetrical HPLC elution profiles and had the highest constant specific activity. Their activity was established both by the standard $A_{340}$ assay using ethanol and using substrates IA and IIA under conditions described herein, but in the absence of serum.

Reconstitution experiments employed inactive serum samples randomly selected from the hospital population exhibiting little or no ADH activity. After the residual background reaction was recorded, a purified ADH isozyme prepared as described in Example 1 was then added and the rate measured as described in part 8 of Example 1. All measurements were made in triplicate.

As shown in Table V, recoveries for both ADH classes in reconstituted serum were >75%. Efforts to increase the sensitivity using more concentrated sera showed that only 50% activity could be recovered when serum was diluted only 10 fold. Importantly, when serum is diluted 50 fold the recovery of activity is constant and, thus the activity observed is proportional to the amount of ADH added over the entire range of activities encountered.

TABLE V

Reconstruction of the Activity of Purified ADH Isozymes in 50-Fold Inactivated Diluted Human Serum.

| Sample No. | ADH Class | Substrate | Rate[a] (nm/min) | Recovery[b] (%) | Coefficient of Variation (%) | n |
|---|---|---|---|---|---|---|
| 1 | I[c] | IA | 1422 | 76.9 | 11.0 | 6 |
| 2 | I[d] | IA | 5.0 | 78.8 | 34 | 5 |
| 3 | I[d] | IA | 36.0 | 81.9 | 5.2 | 5 |
| 4 | I[d] | IA | 286.4 | 60.0 | 7.4 | 8 |
| 5 | II | IIA | 61.2 | 82.0 | 14.5 | 6 |
| 6 | II | IIA | 366 | 83.4 | 7.6 | 10 |
| 7 | II | IIA | 854 | 85.9 | 10.8 | 7 |
| 8 | II | IIA | 1188 | 81.3 | 5.8 | 10 |

[a]Rate measured for purified enzyme in the absence of serum.
[b]Ratio of the rate in serum over the rate in the absence of serum times 100.
[c]Purified Class I $\alpha\beta_1$ isozyme.
[d]Mixture of Class I isozymes from crude liver homogenate.

2. Mixed Reconstitution Procedure

Figure 6:
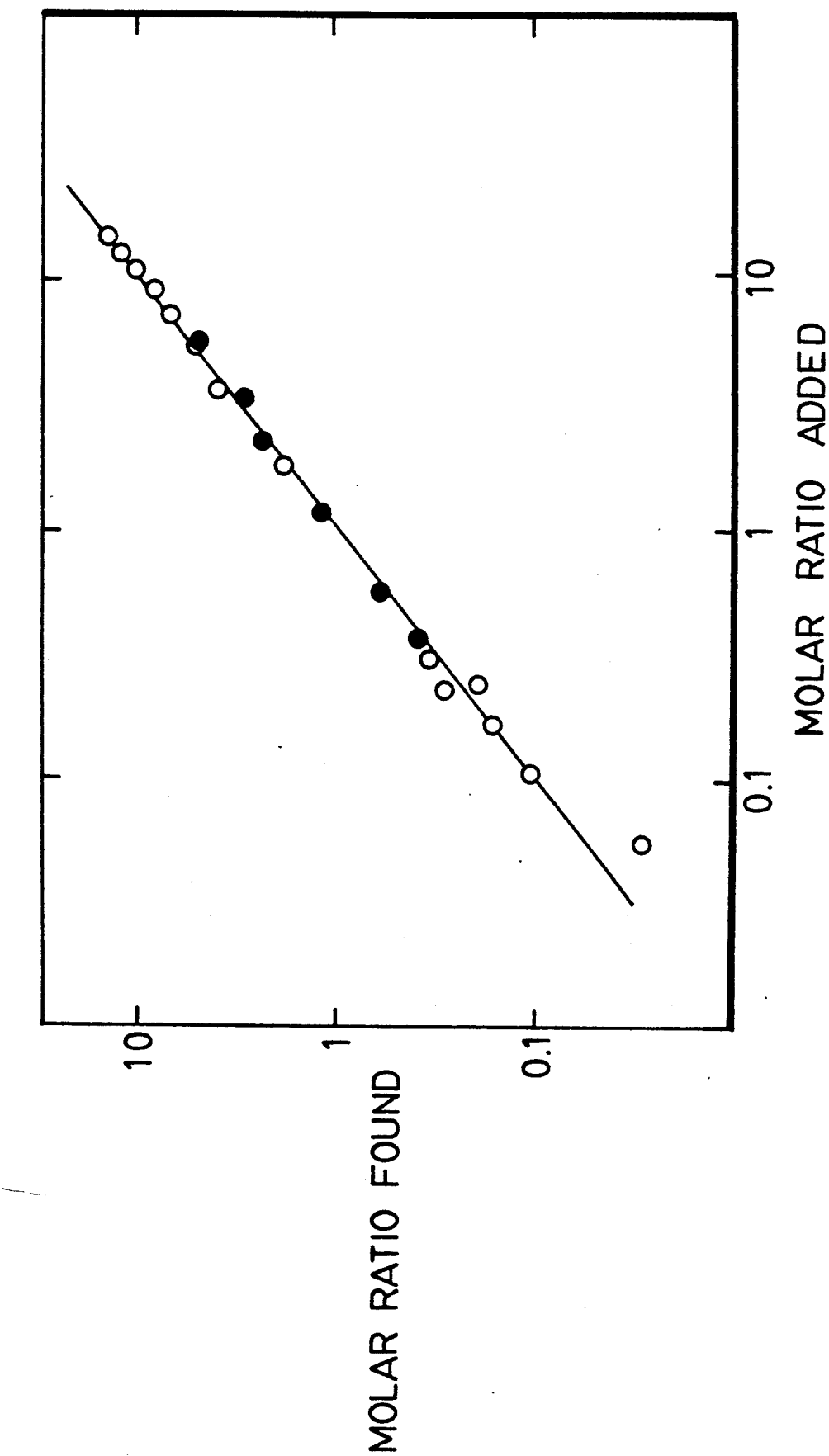
FIG. 6 is a graph of the results from a mixed reconstitution experiment for Class I (A) and Class II (B) ADH. Mixtures of purified Class I and Class II ADH were prepared at different Class I/Class II molar ratios and added to reconstitute inactive sera. The calculated molar ratios from measurements of rates of reactions of the prepared mixtures according to the four-assay procedure were plotted against actual molar ratios of the prepared mixtures.

Mixed reconstitution experiments were carried out on purified Class II ADH with a mixture of Class I ADH to differentiate quantitatively between these activities. Mixtures of purified forms of both ADH classes were prepared at different ration and added to pooled 50-fold diluted ADH-free serum samples (i.e., pooled inactive sera as described in part 1 above). Rates of reaction with IA and IIA as substrates were measured and activities calculated as described in Examples 1, 2 and 4. FIG. 6 shows the results of a representative mixed reconstitution experiment. In FIG. 6, the abscissa is the actual composition of the prepared mixture, expressed as molar ratio of Class I/Class II ADH added to serum, and the ordinate is the composition as calculated from the measured reaction rates. Concentrations of the reference samples, containing pure Class I or II ADH, were calculated on the basis of their activity alone in the presence of serum. Rates in this experiment were between 50 and 1700 nM/minute for both substrates. The range for Class I is 5 to 1000 nM/minute. Open circles are values at a measured constant Class II ADH activity. The closed circles indicate the calculated value of the Class I/Class II ADH molar ratio in the prepared mixture as plotted against the actual value of the molar ratio of the prepared mixture FIG. 6 therefore shows that there was good agreement between the Class I/Class II molar ratio calculated and the known molar ratio of the prepared mixture, indicating the accuracy of the assay.

EXAMPLE 4

The Four-Assay Procedure for Resolution of Class I and Class II ADH Activities in Human Serum.

1. The Procedure

The four-assay procedure measures reaction rates using the fluorometric procedure described in Example 1 for both substrates IA and IIA with and without 0.2 mM 4-MeP. Thus, the rate of conversion of substrate IA to product IB is measured twice in two separate assays, one assay in the presence of 0.2mM 4-MeP and one assay with no inhibitor. Similarly, the rate of conversion of substrate IIA to product IIB is measured in two separate assays, one with 0.2 mM 4-MeP and one with no 4-MeP. The four-assay procedure thus results in a total of four separate assays for each serum sample.

The measured reaction rates, $V_1$ and $V_2$, for substrate IA with and without the inhibitor, respectively, and $V_3$ and $V_4$ for substrate IIA with and without the inhibitor, respectively, are related to the actual Class I and Class II ADH activities, $A_I$, $A_{II}$, and $A_{\beta\beta}$, through the following set of equations:

$$V_1 = A_I + aA_{II} \tag{1a}$$

$$V_2 = bA_I + a(1-c)A_{II} \tag{2a}$$

$$V_3 = A_{II} + dA_I + A_{\beta\beta} \tag{3a}$$

$$V_4 = (1-c)A_{II} + fA_I + eA_{\beta\beta} \tag{4a}$$

where $A_{\beta\beta}$ is $\beta\beta$-ADH activity with IIA as a substrate, constants a, c and f are the same as in the two-assay procedure described in Example 2; b is the Class I activity fraction which is retained in the presence of 0.2 mM 4-MeP (0.025), d is the ratio of specific rates for Class I ADH with IIA and IA as substrates, average value of 0.27; and e is the fraction of $\beta\beta$-ADH activity uninhibited by 0.2 mM 4-MeP, equal to 0.025.

$A_I$, $A_{II}$ and $A_{\beta\beta}$ are obtained by solving three out of four of the above equations, or their linear combinations. Equations (1a), (3a) and (4a) were used routinely for calculations, with the exception of those cases where $V_1$ was comparable to $V_2$ (practically, $V_2 > 0.3 V_1$), indicating very low levels of 4-MeP sensitive (Class I) ADH isozyme relative to Class II ADH. In these cases, errors due to inaccuracy of the constant become significant, and more accurate results are obtained when equation (1a) is replaced by a linear combination of (1a) and (2a):

$$V_1 - V_2 = (1-b)A_I + a(c)A_{II} \tag{5a}$$

The equations were resolved by an iterative method using a spreadsheet program (Appleworks, Apple Computer Inc.) which also served for data storage.

The resultant values of $\beta\beta$-ADH activity, $A_{\beta\beta}$, must be treated cautiously, especially in those cases where its calculated value is much less than the measured $V_3$ rate (i.e. with IIA as substrate and no inhibitor in the assay) In such situations the activity due to Class II and/or Class I will obscure the $\beta\beta$ reaction and magnify experimental errors.

2. Limits of Detection

Using the instrumentation described in Example 1, part 7, reaction rates as low as 6.5 nM/minute for IA and 25 nM/minute for IIA were reproducible. The limits of detection, i.e.. the point at which the fluorescence change after eight minutes becomes twice the noise level, were 1 nM/minute and 5 nM/minute for the two substrates, IA and IIA, respectively. For Class I and Class II isozymes, these limits correspond to concentrations of 0.14 and 0.17 nM, respectively. The sensitivity is limited primarily by serum background fluorescence and cannot be improved significantly by assaying more concentrated sera Overall sensitivity may be increased by utilizing a scanning double monochromator such as a Shimadzu model RF 5000U spectrofluorometer Using such a spectrofluorometer, assay results were obtained with an approximately 20-fold increase in sensitivity and 60-fold increase in speed.

3. Repeatability of Measurements

Repeatability of the ADH activity measurements with both substrates IA and IIA is given in Table VI. Sera were chosen with activities between 6 and 145 nM/minute for Class I ADH and between 25 and 558 nM/minute for Class II, values that encompass most rates encountered thus far in the sera of patients. For these experiments, one operator performed five measurements on each sample. The ADH activity of sera can vary considerably, up to 500 times the limit of detection, and the routine 8 minute recording time in such cases exceeds the recorder span. In such instances the initial rate was calculated from the linear tracing observed for 2 minutes of reaction giving sufficient precision (row 4 of Table VI).

TABLE VI

Between-run Repeatability of Measurements of Substrates

| Substrate | Average rate (nM/min) | Standard Deviation (nM/min) | Coefficient of Variation[c] (%) | n[a] |
|---|---|---|---|---|
| IA | 6.5 | 0.5 | 8.2 | 5 |
| IA | 15.4 | 0.6 | 3.6 | 5 |
| IA | 51.8 | 3.2 | 6.2 | 5 |
| IA[b] | 144.8 | 7.9 | 5.5 | 5 |
| IIA | 25.0 | 3.3 | 13.2 | 5 |
| IIA | 42.5 | 4.9 | 11.6 | 5 |
| IIA | 105.0 | 8.2 | 7.8 | 5 |
| IIA | 424 | 20.0 | 4.7 | 5 |
| IIA | 558 | 26.7 | 4.8 | 5 |

[a]Number of repeat measurements made sequentially by the same operator.
[b]Rates determined from a 2 minutes rather than an 8 minutes reaction.
[c]Standard Deviation/Average Rate 4. Specificity The acid oxidation products of IA and IIA, 4-methoxy-1-naphthoate and 6-methoxy-2-naphthoate, have fluorescent properties very similar to those of the corresponding alcohols, and therefore could potentially interfere with the assay. Therefore, the potential of interference from spontaneous oxidation or that by other oxidoreductases in serum (Wermuth, 1985, in *Enzymology of Carbonyl Metabolism*. (Flynn and Weiner, eds.). Vol. 2. pp. 209-30, A. R. Liss. New York) was examined by testing random serum samples and verifying that the products of the assays are indeed the alcohols IB and IIB and not the acid oxidation products. Assays were allowed to proceed for 1-2 hours (to about 40% completion), and the reaction mixture was then diluted 10-fold into 3 ml of carbonate buffer, pH 10.0, containing 0.5 mM NAD+. An ADH isozyme was then added (up to a concentration of 10 nM), while monitoring the decrease of fluorescence due to aldehyde production. In all 10 samples tested, the fluorescence at 360-370 nm vanished after addition of ADH, demonstrating that the fluorescent product is indeed the expected alcohol. Only upon extended incubation (24 hours) were secondary fluorescent products generated Their spectra correspond to the 1,4- and 2,6-substituted napthoic acids, presumably the result of low level aldehyde dehydrogenase catalyzed oxidation. With serum samples, these acid oxidation products may be avoided by assay reaction times under 24 hours. For analysis of tissues or body fluids other than serum, inhibition with 4-PeP. o-phenanthroline or chromatographic separation of the products may be required to establish that the measurement is specific for the various ADH isoenzyme classes.

5. Normal ADH Levels o In duplicate measurements of serum samples obtained from 17 healthy volunteers no activity toward IA was found Thus, leaving aside activity due to the $\beta\beta$ forms, the normal activity of Class I ADH was <1.0 nM/minute while that of Class II was 15.3 nM/minute (n=17, S.D. 5 nM/minute, range =8.1 to 30.0 nM/minute), clearly well above the limits of detection for this substrate. The activity of these samples towards IIA was insensitive to 4-MeP, but 0.2 mM 4-PeP abolished it, as would be expected for Class II ADH. Based on a $k_{cat}$ of 1500 min.$^{-1}$, the concentration of Class II ADH in normal human serum was calculated to be 0.51±0.22 nM.

In a second group of thirty six sera obtained randomly from the hospital patient population, thirty exhibited an average value of 15±7 nM/minute for IIA but no detectable activity for IA. i.e. less than 1 nM/minute. The remaining six samples were active towards both substrates.

6. Elevated ADH Levels

Sera whose ADH activity was increased beyond those seen normally were selected based on the modified NDMA assay as described in part 7 of Example 1. In approximately 3% of several hundred random hospital patients tested, elevations in ADH activity were observed using the modified NDMA assay described in part 7 of Example 1. These sera with elevated levels (>2 NDMA mU/ml) were then tested by the fluorometric assay described in part 8 of Example 1 using IA as substrate. Class I ADH activity was detected in nearly all of those classified as having elevated ADH levels by the NDMA criterion. The fluorescent reaction product was analyzed and confirmed to be the alcohol ADH product IB. The observed reaction was inhibited >95% by 3 mM 4-MeP; this confirmed that the activity observed was due primarily to Class I ADH. The rate of reduction of IA was also diminished by the addition of high concentrations (>>$K_m$) of typical ADH substrates, e.g., 0.5 mM benzaldehyde or butyraldehyde, presumably due to competition. The serum dilution versus activity curves for sera with relatively high ADH activity were linear over a dilution range of 20-1000 Samples diluted less than 20-fold proved difficult to assay due to background fluorescence and/or significant absorption of the sample. The optimal dilution for routine measurements was approximately 50-fold.

Figure 9:
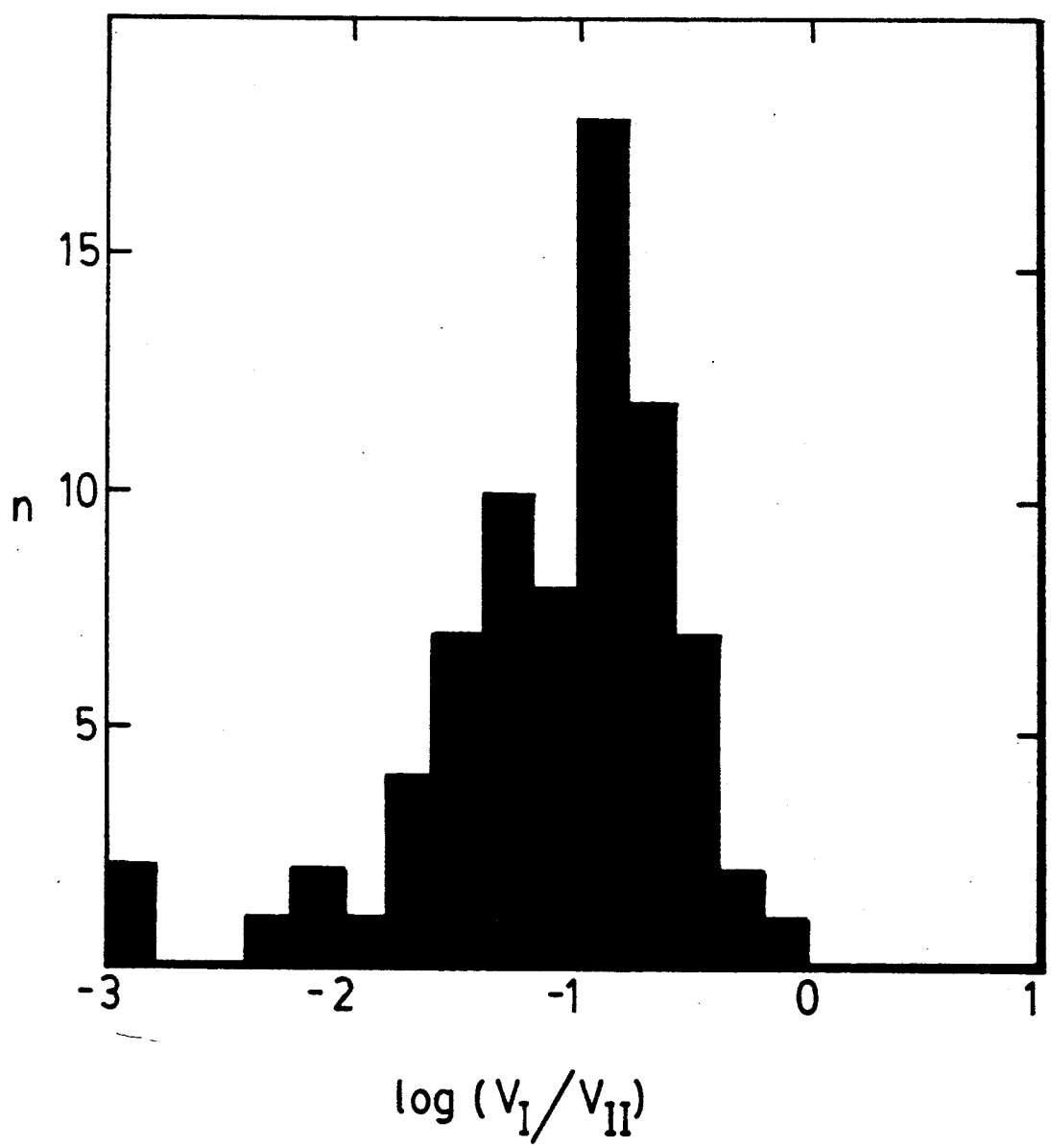
FIG. 9 is a histogram of the ratio of Class I to Class II ADH activities (log ($V_I/V_{II}$)) in 73 serum samples with elevated ADH levels from 15 individuals over a period of 7 weeks.

Seventy-three serum samples from 15 patients in a hospital population showing elevated ADH levels by the NDMA assay were assayed for ADH activity using the four-assay procedure of Example 4. The sera were collected during a period of seven weeks. The results of assaying those sera with elevated ADH levels using this four-assay procedure are shown in FIG. 9. The activities ranged over more than 2 orders of magnitude, and the average ratio of Class I to Class II activities was close to 0.1. Based on their respective averaged $k_{cat}$ values this corresponds to a 2-3 fold molar excess of Class II over Class I ADH. The highest concentration of Class I ADH observed in any serum sample was 300 nM, though there were several instances of values between 200 and 300 nM for both classes.

In nearly all sera measured in which ADH activity was increased, the Class II ADH activity (and concentration) was higher than that of Class I (FIG. 9). The activity of some serum samples was almost exclusively due to Class II ADH. The results to date indicate that Class II ($\eta$) ADH, a relatively unstable isozyme thus far reported to occur in liver only (Biochemistry. 23:6363-6366, 1984, Ditlow et al.), is probably the principal form of human ADH in both normal and pathological sera.

The Class I $\beta\beta$ isozymes reduce IA at a rate much faster than IIA, but unlike Class II they are inhibited readily by 4-MeP. These isozymes did not make a significant contribution to the total activity of any of the sera examined.

EXAMPLE 5

Comparison of the Four-Assay and Two-Assay Procedures

The four-assay procedure of Example 4 is especially useful in that it corrects for the overlap in specificity of the substrates, the relative sensitivity of the two classes to 4-MeP inhibition, and the presence of the Class I $\beta\beta$ isozyme by means of a set of simultaneous equations which are easily solved. However, for nearly all samples, the two-assay procedure of Example 2 using IA in the absence of any ADH inhibitor, and IIA in the presence of 4-MeP as Class I inhibitor is quite satisfactory and is much easier and faster. To examine the validity of the two-assay procedure, the data obtained by the four-assay procedure were recalculated using the equations for the two-assay procedure. FIG. 10 validates the two-assay procedure for most cases. Discrepancies between the results of the two-assay procedure and the four assay are likely to result only in cases of exceptionally high Class II activity relative to Class I activity. Points, for which Class II activity was more than 50 times greater than that for Class I are shown in FIG. 10 as open circles. Such cases would require the two additional rate measurements of the four-assay procedure.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A fluorescence-based method for selectively determining human Class I alcohol dehydrogenase activity in body fluids or tissues comprising:
   (a) measuring the reaction of a non-naturally occurring aromatic aldehyde Class I-selective alcohol dehydrogenase substrate with a sample of the body fluid or tissue, wherein the Class I-selective alcohol dehydrogenase substrate is a compound of the formula;

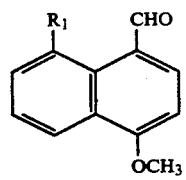

wherein R$_1$ is —H, —OH, —OCH$_3$, —N(CH$_3$)$_2$, or —O(CH$_2$)$_n$CH$_3$ and n is an integer from 1-8, and
   (b) determining the activity of the human Class I alcohol dehydrogenase from the reaction measured in step (a).

2. A fluorescence-based method for selectively determining human Class I alcohol dehydrogenase activity according to claim 1, wherein the Class I-selective alcohol dehydrogenase substrate is a compound of the formula:

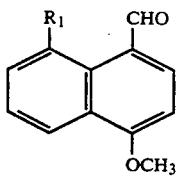

wherein $R_1$ is —H.

3. A fluorescence-based method for selectively determining human Class II alcohol dehydrogenase activity in body fluids or tissues comprising;
(a) measuring the reaction of a non-naturally occurring aromatic aldehyde Class II-selective alcohol dehydrogenase substrate with a sample of the body fluid or tissue, wherein the Class II-selective alcohol dehydrogenase substrate is a compound of the formula:

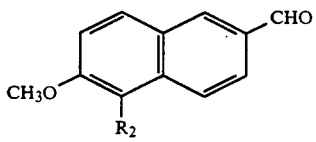

wherein $R_2$ is —H, —OH, —OCH$_3$, —N(CH$_3$)$_2$, or —O(CH$_2$)$_n$CH$_3$ and n is an integer from 1-8, and
(b) determining the activity of the human Class II alcohol dehydrogenase from the reaction measured in step (a).

4. A method for determining Class II alcohol dehydrogenase activity according to claim 3, wherein the Class II alcohol dehydrogenase substrate is a compound of the formula:

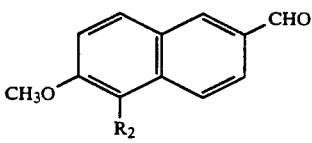

wherein $R_2$ is —H.

5. A fluorescence-based method for selectively determining human Class II alcohol dehydrogenase activity according to claim 3, wherein the activity of the Class II alcohol dehydrogenase is measured with the Class II-selective alcohol dehydrogenase substrate in the presence of an inhibitor of Class I alcohol dehydrogenase.

6. A fluorescence-based method for selectively determining human Class II alcohol dehydrogenase activity according to claim 5, wherein the inhibitor of Class I alcohol dehydrogenase is 4-alkylpyrazole where the alkyl group contains 1 to 2 carbons.

7. A fluorescence-based method for selectively determining human Class II alcohol dehydrogenase activity according to claim 6, wherein the Class II-selective alcohol dehydrogenase substrate is a compound of the formula:

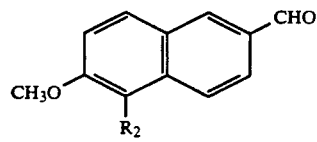

wherein $R_2$ is —H, —OH, —OCH$_3$, —N(CH$_3$)$_2$, or —O(CH$_2$)$_n$CH$_3$ and n is an integer from 1-8.

8. A fluorescence-based method for selectively determining human Class II alcohol dehydrogenase activity according to claim 6, wherein the Class II-selective alcohol dehydrogenase substrate is a compound of the formula:

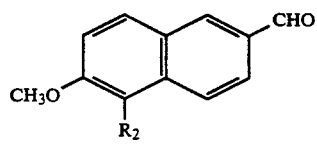

wherein $R_2$ is —H.

9. A fluorescence-based method for selectively determining human Class II alcohol dehydrogenase activity according to claim 8, wherein the inhibitor of Class I alcohol dehydrogenase is 4-methylpyrazole.

10. A method for determining Class I and Class II alcohol dehydrogenase in human serum comprising:
(a) measuring the reaction rate of the reduction of 4-methoxy-1-naphthaldehyde with and without an inhibitor of Class I alcohol dehydrogenase;
(b) measuring the reaction rate of the reduction of 6-methoxy-2-naphthaldehyde with and without an inhibitor of Class I alcohol dehydrogenase; and
(c) determining the activity of Class I and Class II alcohol dehydrogenase using the reaction rates measured in steps (a) and (b).

11. A method according to claim 10 wherein the inhibitor of Class I alcohol dehydrogenase is 4-methylpyrazole.

12. In a method for detecting alcohol dehydrogenase activity in human serum by the steps of (a) measuring the reaction of an alcohol dehydrogenase substrate with a sample of the human serum, and (b) determining the alcohol dehydrogenase activity from the reaction in step (a), the improvement comprising using a methoxynaphthaldehyde compound as alcohol dehydrogenase substrate.

13. A method according to claim 12 wherein the methoxynaphthaldehyde compound is of the formula:

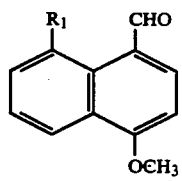

wherein $R_1$ is —H, —OH, —OCH$_3$, —N(CH$_3$)$_2$, or —O(CH$_2$)$_n$CH$_3$ and n is an integer from 1-8.

14. A method according to claim 12 wherein the methoxynaphthaldehyde compound is of the formula:

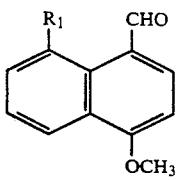
wherein $R_1$ is —H.
15. A method according to claim 12 wherein the methoxynaphthaldehyde compound is of the formula:
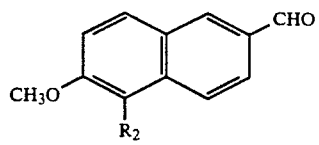
wherein $R_2$ is —H, —OH, —OCH$_3$, —N(CH$_3$)$_2$, or —O(CH$_2$)$_n$CH$_3$ and n is an integer from 1-8.
16. A method according to claim 12 wherein the methoxynaphthaldehyde compound is of the formula:
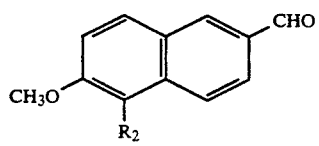
wherein $R_2$ is —H.
* * * * *